United States Patent
Li et al.

(10) Patent No.: US 9,716,235 B2
(45) Date of Patent: Jul. 25, 2017

(54) 9,10-BIS[2-(P-SUBSTITUTED PHENYL)PYRIMIDIN-4-YL] ANTHRACENE COMPOUNDS, METHODS OF PREPARING THE SAME, ORGANIC ELECTROLUMINESCENT DEVICES AND ORGANIC ELECTROLUMINESCENT DISPLAY APPARATUS

(71) Applicant: BOE TECHNOLOGY GROUP CO., LTD., Beijing (CN)

(72) Inventors: Na Li, Beijing (CN); Yansong Li, Beijing (CN); Lujiang Huangfu, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 654 days.

(21) Appl. No.: 14/361,699

(22) PCT Filed: Nov. 6, 2013

(86) PCT No.: PCT/CN2013/086614
§ 371 (c)(1),
(2) Date: May 29, 2014

(87) PCT Pub. No.: WO2015/003441
PCT Pub. Date: Jan. 15, 2015

(65) Prior Publication Data
US 2015/0214487 A1 Jul. 30, 2015

(30) Foreign Application Priority Data
Jul. 9, 2013 (CN) .......................... 2013 1 0286918

(51) Int. Cl.
| | | |
|---|---|---|
| H01L 51/54 | (2006.01) | |
| C09K 11/06 | (2006.01) | |
| H01L 51/00 | (2006.01) | |
| C07D 239/26 | (2006.01) | |
| C07C 249/02 | (2006.01) | |
| H01L 51/50 | (2006.01) | |
| H01L 51/52 | (2006.01) | |

(52) U.S. Cl.
CPC ........ *H01L 51/0067* (2013.01); *C07C 249/02* (2013.01); *C07D 239/26* (2013.01); *C09K 11/06* (2013.01); *H01L 51/0052* (2013.01); C09K 2211/1074 (2013.01); H01L 51/5012 (2013.01); H01L 51/5056 (2013.01); H01L 51/5072 (2013.01); H01L 51/5096 (2013.01); H01L 51/5206 (2013.01); H01L 51/5221 (2013.01); H01L 51/5231 (2013.01)

(58) Field of Classification Search
CPC ... C07C 249/00; C07C 249/02; C07D 239/00; C07D 239/02; C07D 239/24; C07D 239/26; C09K 11/06; C09K 2211/00; C09K 2211/1074; H01L 51/0032; H01L 51/0052; H01L 51/0067; H01L 51/0062; H01L 51/0072; H01L 51/50; H01L 51/5012; H01L 51/5056; H01L 51/5072; H01L 51/5096; H01L 51/5206; H01L 51/5221; H01L 51/5231; H01L 51/5016
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

2013/0087771 A1* 4/2013 Qiu ..................... H01L 51/0052
257/40

FOREIGN PATENT DOCUMENTS

| CN | 101144012 A | 3/2008 |
|---|---|---|
| CN | 102936184 A | 2/2013 |
| CN | 103130724 A | 5/2013 |
| JP | 2009277986 A | 11/2009 |
| KR | 20120041110 A | 4/2012 |

OTHER PUBLICATIONS

PCT International Search Report for PCT Counterpart Application No. PCT/CN2013/086614 Containing International Search Report with full English translation, 5 pgs. (Aug. 22, 2014).
PCT Written Opinion of the International Searching Authority for PCT Counterpart Application No. PCT/CN2013/086614 with full English translation, 8 pgs. (Aug. 25, 2014).

(Continued)

*Primary Examiner* — Andrew L Bohaty
(74) *Attorney, Agent, or Firm* — Blakely, Sokoloff, Taylor & Zafman LLP

(57) ABSTRACT

The invention relates to organic electroluminescent materials and provides 9,10-bis[2-(p-substituted phenyl)pyrimidin-4-yl] anthracene compounds and methods of preparing the same, organic electroluminescent devices comprising the compounds, and organic electroluminescent display apparatus comprising the devices. The compounds of the invention are easy to be synthesized and can be used as blue-phosphorescent organic electroluminescent materials. Due to the inherent ability of the materials to block holes, there is no need to arrange a hole-blocking layer between a light-emitting layer and an electron transport layer, which simplifies the manufacturing process of full color display panels of organic electroluminescent display apparatus and reduces the manufacture cost and time. The organic electroluminescent devices made from the materials exhibit high luminous efficiency.

14 Claims, 2 Drawing Sheets

(56) References Cited

OTHER PUBLICATIONS

PCT International Preliminary Report on Patentability for PCT Application No. PCT/CN2013/086614 with full English translation, 10 pgs. (Jan. 12, 2016).
Yuji Suzaki, et al., "Tweezers-like aromatic molecules and their luminescent properties depending on the structures," Tetrahedron Letters, vol. 52, Issue 30, pp. 3883-3885 (Jul. 27, 2011).
First Office Action for corresponding Chinese Patent Application No. 201310286918.2, 5 pages, (Oct. 10, 2014).

* cited by examiner

9,10-BIS[2-(P-SUBSTITUTED PHENYL)PYRIMIDIN-4-YL] ANTHRACENE COMPOUNDS, METHODS OF PREPARING THE SAME, ORGANIC ELECTROLUMINESCENT DEVICES AND ORGANIC ELECTROLUMINESCENT DISPLAY APPARATUS

CROSS-REFERENCE TO RELATED APPLICATIONS

This patent application is a U.S. National Phase Application under 35 U.S.C. §371 of International Application No. PCT/CN2013/086614, filed Nov. 6, 2013, entitled 9,10-BIS [2-(P-SUBSTITUTED PHENYL)PYRIMIDIN-4-YL] ANTHRACENE COMPOUNDS, METHODS OF PREPARING THE SAME, ORGANIC ELECTROLUMINESCENT DEVICES AND ORGANIC ELECTROLUMINESCENT DISPLAY APPARATUS, which claims priority to Chinese Patent Application No. 201310286918.2, filed Jul. 9, 2013.

FIELD OF THE INVENTION

The present invention relates to the technical field of organic electroluminescent materials, particularly to pyrimidinyl anthracene compounds and methods of preparing the same, organic electroluminescent devices comprising light-emitting layers made from the compounds, and organic electroluminescent display apparatus comprising the organic electroluminescent devices.

BACKGROUND OF THE INVENTION

Organic light-emitting diodes (OLEDs) are light-emitting diodes including light-emitting layers made from organic materials. The research and development of organic materials is an important branch of the research and development of light-emitting diodes. The known organic electroluminescent materials include phosphorescent materials and fluorescent materials. OLEDs mainly based on phosphorescent mechanism have attracted tremendous attention recently, because phosphorescent materials can keep luminance for a considerable long time after excited, and the quantum efficiency thereof (theoretical value may be up to 100%) is four times of that of fluorescent materials.

However, there are two main problems involved in the phosphorescent organic electroluminescent devices:
1) compared with the known fluorescent organic molecules, it is relatively difficult to synthesize the phosphorescent organic molecules, particularly the phosphorescent organic molecules emitting blue or green light; and
2) a hole-blocking layer (hereinafter referred to as HBL) needs to be arranged between a light-emitting layer and an electron transport layer (hereinafter referred to as ETL), in order to prevent impurity and extinction of light caused by diffusion of the excited state energy from the light-emitting layer to other layers.

Nowadays, full-color display panels of the OLEDs are made mainly by arranging red, green and blue pixels in a "side-by-side" array. However, the development of blue phosphorescent pixels badly lags behind other phosphorescent pixels, so that it is still impossible to use exclusively phosphorescent devices in the "side-by-side" pixel array. That is, the phosphorescent pixels need to be used in combination with the fluorescent pixels, and thus an evaporation chamber for deposition of an HBL has to be included in mass production. In such a case, the process steps cannot be integrated, which not only increases the manufacture cost and time, but also makes the manufacturing process complex.

SUMMARY OF THE INVENTION

An object of the present invention is to solve the problem that an HBL needs to be arranged between a light-emitting layer and an ETL in the existing phosphorescent organic electroluminescent materials emitting blue light.

This object is achieved by providing a 9,10-bis[2-(p-substituted phenyl)pyrimidin-4-yl] anthracene compound represented by the following formula:

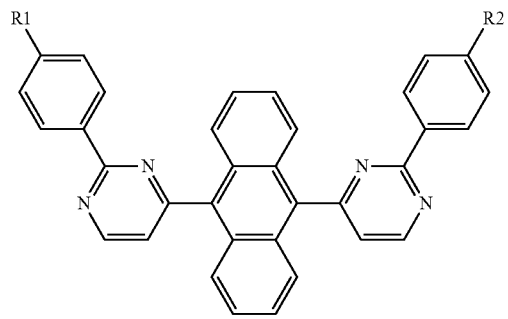

wherein R1 and R2, which may be identical or different, are each individually selected from any one of:
hydrogen, carboxyl, cyano, nitro,
paraffinic alkyl having 1 to 20 carbon atoms,
cyclic alkyl having 3 to 20 carbon atoms,
paraffinic alkoxyl having 1 to 20 carbon atoms,
aromatic hydrocarbyl having 6 to 50 ring carbon atoms,
aryloxy having 5 to 50 ring atoms, and
an ester group having 2 to 20 carbon atoms.

Herein, the term "paraffinic alkyl having 1 to 20 carbon atoms" refers to "unsubstituted C1-C20 linear or branched alkyl" or "substituted C1-C20 linear or branched alkyl".

The term "unsubstituted C1-C20 linear or branched alkyl" refers to C1-C20 linear or C3-C20 branched alkyl without any substituent, preferably C1-C12 linear or C3-C12 branched alkyl, more preferably C1-C8 linear or C3-C8 branched alkyl, and most preferably C1-C6 linear or C3-C6 branched alkyl. For example, it is preferably methyl, ethyl, propyl, isopropyl, n-butyl, sec-butyl, isobutyl, tert-butyl, n-pentyl, isopentyl, neopentyl, n-hexyl, n-heptyl, or n-octyl.

The term "substituted C1-C20 linear or branched alkyl" refers to C1-C20 linear or C3-C20 branched alkyl having 1 to 3 substituents, preferably C1-C12 linear or C3-C12 branched alkyl, more preferably C1-C8 linear or C3-C8 branched alkyl, most preferably C1-C6 linear or C3-C6 branched alkyl. The said 1 to 3 substituents are selected from hydroxyl, halogen, amino, carboxyl, cyano, nitro, pyrrolyl, naphthyl, and substituted or unsubstituted phenyl. The substituted phenyl refers to a benzene ring substituted by methyl, hydroxyl, halogen, amino, carboxyl, cyano or nitro.

The substituted C1-C20 linear or branched alkyl includes, for example, C1-C20 linear or C3-C20 branched alkyl substituted by hydroxyl, halogen, amino, cyano, nitro, phenyl, etc.

Preferable examples of the substituted C1-C20 linear or branched alkyl include, but not limited to, C1-C4 alkyl substituted by hydroxyl, such as hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-tert-butyl, 1,2,3-trihydroxypropyl; C1-C4 alkyl substituted by halogen, such as fluoromethyl, chloromethyl, 1-chloroethyl, 2-chloroethyl, 2-chloroisobutyl, 1,2-dichloroethyl, 1,3-dichloroisopropyl, 2,3-dichloro-tert-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-tert-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-tert-butyl, 1,2,3-triiodopropyl; C1-C4 alkyl substituted by amino, such as aminomethyl, 1-aminoethyl, 2-aminoethyl, 2-aminoisobutyl, 1,2-diaminoethyl, 1,3-diaminoisopropyl, 2,3-diamino-tert-butyl, 1,2,3-triaminopropyl; C1-C4 alkyl substituted by cyano, such as cyanomethyl, 1-cyanoethyl, 2-cyanoethyl, 2-cyanoisobutyl, 1,2-dicyanoethyl, 1,3-dicyanoisopropyl, 2,3-dicyano-tert-butyl, 1,2,3-tricyanopropyl; C1-C4 alkyl substituted by nitro, such as nitromethyl, 1-nitroethyl, 2-nitroethyl, 2-nitroisobutyl, 1,2-dinitroethyl, 1,3-dinitroisopropyl, 2,3-dinitro-tert-butyl, 1,2,3-trinitropropyl; C1-C4 alkyl substituted by phenyl, such as benzyl, 1-phenylethyl, 2-phenylethyl, 1-phenylisopropyl, 2-phenylisopropyl, phenyl-tert-butyl, triphenylmethyl; C1-C4 alkyl substituted by naphthyl, such as α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl; C1-C4 alkyl substituted by pyrrolyl, such as 1-pyrrolylmethyl, 2-(1-pyrrolyl)ethyl; C1-C4 alkyl substituted by substituted phenyl, such as p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-chloro-2-phenylisopropyl.

Herein, the term "cyclic alkyl having 3 to 20 carbon atoms" refers to "unsubstituted C3-C20 saturated alicyclic hydrocarbyl" or "substituted C3-C20 saturated alicyclic hydrocarbyl"; preferably "unsubstituted C6-C10 saturated alicyclic hydrocarbyl" or "substituted C6-C10 saturated alicyclic hydrocarbyl".

The term "substituted C3-C20 saturated alicyclic hydrocarbyl" refers to C3-C20 saturated alicyclic hydrocarbyl having 1 to 3 substituents selected from C1-C4 alkyl, hydroxyl, halogen, amino, carboxyl, cyano and nitro. The term "substituted C6-C10 saturated alicyclic hydrocarbyl" refers to C6-C10 saturated alicyclic hydrocarbyl having 1 to 3 substituents selected from C1-C4 alkyl, hydroxyl, halogen, amino, carboxyl, cyano and nitro.

Examples of the unsubstituted C3-C20 saturated alicyclic hydrocarbyl include, but not limited to, cyclopropyl, cyclobutyl, cyclopentyl, cyclohexyl, norbornyl (i.e., bicyclo[2.2.1]heptyl), adamantyl or cycloeicosyl.

Preferable examples of the substituted C3-C20 saturated alicyclic hydrocarbyl include 2-fluorocyclopropyl, 3-hydroxylcyclobutyl, 3-aminocyclopentyl, 4-methylcyclohexyl, and 1,3,5-tribromoadamantyl.

Herein, the term "paraffinic alkoxyl having 1 to 20 carbon atoms" refers to "C1-C20 paraffinic alkyl-O—", wherein the definition of the "C1-C20 paraffinic alkyl" is the same as that of the "paraffinic alkyl having 1 to 20 carbon atoms".

For example, particular examples of the C1-C20 paraffinic alkyl include unsubstituted C1-C8 alkyl, such as methyl, ethyl, propyl, isopropyl, n-butyl, sec-butyl, isobutyl, tert-butyl, n-pentyl, n-hexyl, n-heptyl, or n-octyl; C1-C4 alkyl substituted by hydroxyl, such as hydroxymethyl, 1-hydroxyethyl, 2-hydroxyethyl, 2-hydroxyisobutyl, 1,2-dihydroxyethyl; C1-C4 alkyl substituted by halogen, such as fluoromethyl, 1,3-dichloroisopropyl, 2,3-dichloro-tert-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-tert-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-tert-butyl, 1,2,3-triiodopropyl; C1-C4 alkyl substituted by amino, such as aminomethyl, 1-aminoethyl, 2-aminoethyl, 2-aminoisobutyl, 1,2-diaminoethyl, 1,3-diaminoisopropyl, 2,3-diamino-tert-butyl, 1,2,3-triaminopropyl; C1-C4 alkyl substituted by cyano, such as cyanomethyl, 1-cyanoethyl, 2-cyanoethyl, 2-cyanoisobutyl, 1,2-dicyanoethyl, 1,3-dicyanoisopropyl, 2,3-dicyano-tert-butyl, 1,2,3-tricyanopropyl; C1-C4 alkyl substituted by nitro, such as nitromethyl, 1-nitroethyl, 2-nitroethyl, 2-nitroisobutyl, 1,2-dinitroethyl, 1,3-dinitroisopropyl, 2,3-dinitro-tert-butyl, 1,2,3-trinitropropyl; C1-C4 alkyl substituted by phenyl, such as benzyl, 1-phenylethyl, 2-phenylethyl, 1-phenylisopropyl, 2-phenylisopropyl, phenyl-tert-butyl, triphenylmethyl; C1-C4 alkyl substituted by naphthyl, such as α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl; C1-C4 alkyl substituted by pyrrolyl, such as 1-pyrrolylmethyl, 2-(1-pyrrolyl)ethyl; C1-C4 alkyl substituted by substituted phenyl, such as p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-chloro-2-phenylisopropyl, etc.

Herein, the term "aromatic hydrocarbyl having 6 to 50 ring carbon atoms" refers to a single benzene ring, a polybenzene ring structure in which two or more benzene rings are connected by single bond(s), or a fused ring structure in which two or more benzene rings are fused at two or more positions. Aromatic carbon rings having 6 to 30 ring carbon atoms are preferable, and particular examples thereof include, but not limited to, phenyl, biphenyl, terphenyl, naphthyl, fluorenyl, anthryl, naphthacenyl, etc. The aromatic hydrocarbyl may be substituted by C1-C4 linear or branched alkyl, or by phenyl substituted with C1-C4 linear or branched alkyl.

Preferably, the aromatic hydrocarbyl having 6 to 50 ring carbon atoms is any one of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthryl, 4-methyl-biphenyl, 4'-tert-butyl-p-terphenyl-4-yl.

Herein, the term "aryloxy having 5 to 50 ring atoms" refers to a group in which an oxygen atom is connected to a ring carbon atom of an aromatic hydrocarbon, or to a ring atom of a heteroaromatic hydrocarbon. Said aromatic hydrocarbon ring refers to an aromatic hydrocarbon type carbon ring having 6 to 50 ring carbon atoms, including a single benzene ring, a polybenzene ring structure in which two or more benzene rings are connected by single bond(s), or a fused ring structure in which two or more benzene rings are fused at two or more positions. Aromatic hydrocarbon type carbon rings having 6 to 30 ring carbon atoms are preferable, and particular examples thereof include, but not limited to, phenyl, biphenyl, terphenyl, naphthyl, fluorenyl, anthryl, naphthacenyl, pyrenyl, picenyl, etc. The aromatic hydrocarbon type carbon ring may be substituted by C1-C4 linear or branched alkyl, or by phenyl substituted with C1-C4 linear or branched alkyl. Said heteroaromatic hydrocarbon ring refers to a single ring or a fused ring structure comprising at least one unsaturated double bond and heteroatom selected from O, N and S in the ring(s), preferably a heteroaromatic ring having 5-20 ring atoms, more preferably a heteroaromatic ring having 5-14 ring atoms; and particular examples thereof include, but not limited to, pyrrole, pyridine, indole, furan, pyran, benzofuran, quinoline, quinoxaline, carbazole, phenanthridine, acridine, phenanthroline, phenazine, phenothiazine, phenoxazine ring, etc.

Preferable examples of the aromatic hydrocarbon type carbon ring are phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthryl, 4'-methyl-biphenyl, 4'-tert-butyl-p-terphenyl-4-yl, etc.

Preferable example of the heteroaromatic hydrocarbon ring is any one of 2-pyrrolyl, 3-pyrrolyl, 5-pyridinyl, 6-pyridinyl, 2-pyridinyl, 3-pyridinyl, 4-pyridinyl, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-furanyl, 3-furanyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalyl, 5-quinoxalyl, 6-quinoxalyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthrolin-2-yl, 1,7-phenanthrolin-3-yl, 1,7-phenanthrolin-4-yl, 1,7-phenanthrolin-5-yl, 1,7-phenanthrolin-6-yl, 1,7-phenanthrolin-8-yl, 1,7-phenanthrolin-9-yl, 1,7-phenanthrolin-10-yl, 1,8-phenanthrolin-2-yl, 1,8-phenanthrolin-3-yl, 1,8-phenanthrolin-4-yl, 1,8-phenanthrolin-5-yl, 1,8-phenanthrolin-6-yl, 1,8-phenanthrolin-7-yl, 1,8-phenanthrolin-9-yl, 1,8-phenanthrolin-10-yl, 1,9-phenanthrolin-2-yl, 1,9-phenanthrolin-3-yl, 1,9-phenanthrolin-4-yl, 1,9-phenanthrolin-5-yl, 1,9-phenanthrolin-6-yl, 1,9-phenanthrolin-7-yl, 1,9-phenanthrolin-8-yl, 1,9-phenanthrolin-10-yl, 1,10-phenanthrolin-2-yl, 1,10-phenanthrolin-3-yl, 1,10-phenanthrolin-4-yl, 1,10-phenanthrolin-5-yl, 2,9-phenanthrolin-1-yl, 2,9-phenanthrolin-3-yl, 2,9-phenanthrolin-4-yl, 2,9-phenanthrolin-5-yl, 2,9-phenanthrolin-6-yl, 2,9-phenanthrolin-7-yl, 2,9-phenanthrolin-8-yl, 2,9-phenanthrolin-10-yl, 2,8-phenanthrolin-1-yl, 2,8-phenanthrolin-3-yl, 2,8-phenanthrolin-4-yl, 2,8-phenanthrolin-5-yl, 2,8-phenanthrolin-6-yl, 2,8-phenanthrolin-7-yl, 2,8-phenanthrolin-9-yl, 2,8-phenanthrolin-10-yl, 2,7-phenanthrolin-1-yl, 2,7-phenanthrolin-3-yl, 2,7-phenanthrolin-4-yl, 2,7-phenanthrolin-5-yl, 2,7-phenanthrolin-6-yl, 2,7-phenanthrolin-8-yl, 2,7-phenanthrolin-9-yl, 2,7-phenanthrolin-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, and 4-tert-butyl-3-indolyl.

Herein, the term "ester group having 2 to 20 carbon atoms" refers to such a group that may be represented by "C1-C19 alkyl-OC(O)—", wherein the C1-C19 alkyl may be linear, branched, or cyclic alkyl. Said ester group having 2 to 20 carbon atoms is preferably a —OC(O)— group connected with C1-C18 alkyl, more preferably C1-C12 alkyl, and most preferably C1-C8 alkyl. Said linear, branched, or cyclic alkyl may be optionally substituted by 1 to 3 substituents selected from hydroxyl, halogen, amino, carboxyl, cyano and nitro. Preferable examples of the ester group having 2 to 20 carbon atoms include any one of methyl ester group, ethyl ester group, propyl ester group, isopropyl ester group, n-butyl ester group, sec-butyl ester group, isobutyl ester group, n-pentyl ester group, n-hexyl ester group, n-heptyl ester group, and n-octyl ester group.

The object of the present invention also includes providing a simple method for preparation of organic electroluminescent materials, so as to overcome the current difficulties encountered in synthesis of the organic electroluminescent materials emitting blue light.

Such an object is achieved by providing a method of preparing the 9,10-bis[2-(p-substituted phenyl)pyrimidin-4-yl] anthracene compound represented by the aforesaid formula, comprising the following steps: reacting p-substituted benzamide with formamide to produce an intermediate; and reacting the intermediate with 9,10-diacetylanthracene to produce said 9,10-bis[2-(p-substituted phenyl)pyrimidin-4-yl] anthracene compound.

In order to solve the problem that the existing organic luminescent devices need an HBL arranged between a light-emitting layer and an ETL, the object of the present invention further includes providing an organic luminescent device without the need to arrange such an HBL between a light-emitting layer and an ETL.

Such an object is achieved by providing an organic luminescent device comprising a cathode, an anode, and a light-emitting layer arranged between said cathode and anode, wherein said light-emitting layer comprises the 9,10-bis[2-(p-substituted phenyl)pyrimidin-4-yl] anthracene compound.

Preferably, said organic luminescent device also comprises a hole transport layer and an electron transport layer (ETL), wherein the hole transport layer is arranged between the anode and the light-emitting layer, and the ETL is arranged between the cathode and the light-emitting layer.

The 9,10-bis[2-(p-substituted phenyl)pyrimidin-4-yl] anthracene compounds according to the present invention can be used as organic electroluminescent materials. Since such compounds per se have an ability to block holes, there is no need to arrange an HBL between the light-emitting layer and the ETL, and thus the evaporation chamber for deposition of the HBL is no longer needed in mass production of full color display panels of organic electroluminescent display apparatus. Therefore, the present invention makes it practical to integrate the manufacturing process of full color display panels of organic electroluminescent display apparatus, thereby reducing the manufacture cost and time. In addition, the organic electroluminescent devices made from the 9,10-bis[2-(p-substituted phenyl)pyrimidin-4-yl] anthracene compounds according to the present invention exhibit high luminous efficiency. Furthermore, the methods of preparing the 9,10-bis[2-(p-substituted phenyl)pyrimidin-4-yl] anthracene compounds according to the present invention are simple and readily applicable.

DETAILED DESCRIPTION OF CERTAIN EMBODIMENTS

Figure 1:
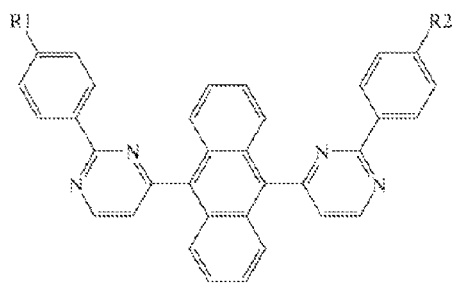
FIG. 1 shows the formula of 9,10-bis[2-(p-substituted phenyl)pyrimidin-4-yl] anthracene compounds according to the present invention.

In order to make those skilled in the art have a better understanding of the technical solution of the present invention, more detailed description is provided below with reference to specific embodiments and the accompanying drawings.

The present invention provides a 9,10-bis[2-(p-substituted phenyl)pyrimidin-4-yl] anthracene compound having the following formula:

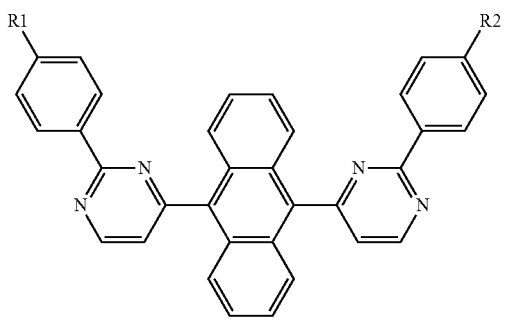

wherein R1 and R2, which may be identical or different, are each individually selected from any one of:
hydrogen, carboxyl, cyano, nitro,
substituted or unsubstituted paraffinic alkyl having 1 to 20 carbon atoms,
substituted or unsubstituted cyclic alkyl having 3 to 20 carbon atoms,
paraffinic alkoxyl having 1 to 20 carbon atoms,
aromatic hydrocarbyl having 6 to 50 ring carbon atoms,
aryloxy having 5 to 50 ring atoms, and
an ester group having 2 to 20 carbon atoms.

According to preferable embodiments of the present invention, R1 and R2 of the compound are each independently selected from the following groups:

C1-C20 linear alkyl or C3-C20 branched alkyl, which may be optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;

C3-C20 cyclic alkyl, which may be optionally substituted by 1 to 3 substituents selected from C1-C4 alkyl, hydroxyl, halogen, amino, carboxyl, cyano and nitro;

C1-C20 paraffinic alkoxyl, in which the C1-C20 paraffinic alkyl may be optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;

aromatic hydrocarbyl having 6 to 50 ring carbon atoms, which may be optionally substituted by C1-C4 linear or branched alkyl, or by phenyl substituted with C1-C4 linear or branched alkyl;

aromatic hydrocarbonoxy having 6 to 50 ring carbon atoms, in which the carbon ring of the aromatic hydrocarbon may be optionally substituted by C1-C4 linear or branched alkyl, or by phenyl substituted with C1-C4 linear or branched alkyl;

heteroaromatic hydrocarbonoxy having 5 to 50 ring atoms, wherein the heteroaromatic hydrocarbon ring comprises at least one unsaturated double bond and heteroatom selected from O, N and S, and the ring carbon atom(s) of the heteroaromatic hydrocarbon ring may be optionally substituted by C1-C4 linear or branched alkyl, or by phenyl substituted with C1-C4 linear or branched alkyl; and an ester group having 2 to 20 carbon atoms, which preferably is C1-C18 alkyl-OC(O)—, wherein the C1-C18 alkyl is a linear, branched, or cyclic alkyl optionally substituted by 1 to 3 substituents selected from hydroxyl, halogen, amino, carboxyl, cyano and nitro.

Preferably, the aromatic hydrocarbyl having 6 to 50 ring carbon atoms (or the aromatic hydrocarbyl of said aromatic hydrocarbonoxy) is selected from phenyl, a polybenzene ring group in which 2-8 benzene rings are connected by single bond(s), or a fused ring group in which 2-10 benzene rings are fused at two or more positions. Further preferably, the aromatic hydrocarbyl is an aromatic hydrocarbon group having 6-30 ring carbon atoms, which may be selected from phenyl, a polybenzene ring group in which 2-5 (preferably 2-4) benzene rings are connected by single bond(s), or a fused ring group in which 2-8 (preferably 2-5) benzene rings are fused at two or more positions, and may be optionally substituted by C1-C4 linear or branched alkyl.

Preferably, the "heteroaromatic hydrocarbon having 5 to 50 ring atoms" comprises one or two heteroatom(s) selected from O, N and S and at least one unsaturated double bond in the heteroaromatic hydrocarbon ring(s), more preferably, at least two unsaturated double bond which may be conjugated or not. The heteroaromatic hydrocarbon group preferably has 5 to 20 ring atoms, more preferably 5 to 14 ring atoms. The heteroaromatic hydrocarbon group may be optionally substituted by C1-C4 linear or branched alkyl.

According to more preferable embodiments of the present invention, R1 and R2 of the compound are each independently selected from the following groups:

C1-C12, preferably C1-C8, more preferably C1-C6 linear or branched alkyl, which may be optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;

C3-C12, preferably C3-C8, more preferably C3-C6 cyclic alkyl, which may be optionally substituted by 1 to 3 substituents selected from C1-C4 alkyl, hydroxyl, halogen, amino, carboxyl, cyano and nitro;

C1-C12, preferably C1-C8, more preferably C1-C6 paraffinic alkoxyl, in which the paraffinic alkyl may be optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;

aromatic hydrocarbyl having 6 to 30 ring carbon atoms selected from phenyl, a polybenzene group in which 2-5 (preferably 2-4) benzene rings are connected by single bond(s), or a fused group in which 2-8 (preferably 2-5) benzene rings are fused at two or more positions, for example, an aromatic hydrocarbon group selected from phenyl, biphenyl, terphenyl, quaterphenyl, naphthyl, fluorenyl, anthryl, naphthacenyl, phenanthryl, perylenyl, picenyl and pyrenyl, wherein the phenyl, the polybenzene group or the fused group may be optionally substituted by C1-C4 linear or branched alkyl;

aromatic hydrocarbonoxy having 6-30 ring carbon atoms selected from phenyl-O—, polybenzene group-O—, or fused group-O—, wherein the polybenzene group is a group in which 2-5 (preferably 2-4) benzene rings are connected by single bond(s), the fused group is a group in which 2-8 (preferably 2-5) benzene rings are fused at two or more positions, and wherein the phenyl, the polybenzene group or the fused group may be optionally substituted by C1-C4 linear or branched alkyl;

heteroaromatic hydrocarbonoxy having 5 to 20 ring atoms, in which the heteroaromatic hydrocarbon ring comprises at least two unsaturated double bond and one or two heteroatom(s) selected from O, N and S, and the ring carbon atom(s) of the heteroaromatic hydrocarbon ring may be optionally substituted by C1-C4 linear or branched alkyl. Particularly preferable examples thereof are selected from pyrrolyl, pyridinyl, indolyl, furanyl, pyranyl, benzofuranyl, quinolyl, quinoxalinyl, carbazolyl, phenanthridinyl, acridinyl, phenanthrolinyl, phenazinyl, phenothiazinyl, and phenoxazinyl; and C1-C12 alkyl-OC(O)—, preferably C1-C8 alkyl-OC(O)—, more preferably C3-C6 alkyl-OC(O)—, in which the alkyl is a linear, branched, or cyclic alkyl optionally substituted by 1 to 3 substituents selected from hydroxyl, halogen, amino, carboxyl, cyano and nitro.

Preferably, the unsubstituted paraffinic alkyl having 1 to 20 carbon atoms is any one of methyl, ethyl, propyl, isopropyl, n-butyl, sec-butyl, isobutyl, tert-butyl, n-pentyl, n-hexyl, n-heptyl, and n-octyl.

Preferably, the substituted paraffinic alkyl having 1 to 20 carbon atoms is any one of hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-tert-butyl, 1,2,3-trihydroxypropyl, fluoromethyl, chloromethyl, 1-chloroethyl, 2-chloroethyl, 2-chloroisobutyl, 1,2-dichloroethyl, 1,3-dichloroisopropyl, 2,3-dichloro-tert-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-tert-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-tert-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-tert-butyl, 1,2,3-triaminopropyl, benzyl, 1-phenylethyl, 2-phenylethyl, 1-phenylisopropyl, 2-phenylisopropyl, phenyl-tert-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-chloro-2-phenylisopropyl, and triphenylmethyl.

Preferably, the unsubstituted cyclic alkyl having 3 to 20 carbon atoms is any one of cyclopropyl, cyclobutyl, cyclopentyl, cyclohexyl, adamantyl, norbornyl and cycloeicosyl.

Preferably, the substituted cyclic alkyl having 3 to 20 carbon atoms is any one of 2-fluorocyclopropyl, 3-hydroxycyclobutyl, 3-aminocyclopentyl, 4-methylcyclohexyl, and 1,2,3-tribromoadamantyl;

Preferably, the alkyl of the paraffinic alkoxyl having 1 to 20 carbon atoms is any one of methyl, ethyl, propyl, isopropyl, n-butyl, sec-butyl, isobutyl, tert-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dichloroisopropyl, 2,3-dichloro-tert-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-tert-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-tert-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-tert-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-tert-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-tert-butyl, and 1,2,3-trinitropropyl.

Preferably, the aromatic hydrocarbyl having 6 to 50 ring carbon atoms is any one of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthryl, 4-methyl-biphenyl, 4'-tert-butyl-p-terphenyl-4-yl.

Preferably, the aromatic group of the aryloxy having 5 to 50 ring atoms is any one of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthryl, 4'-methyl-biphenyl, 4'-tert-butyl-p-terphenyl-4-yl, 2-pyrrolyl, 3-pyrrolyl, 5-pyridinyl, 6-pyridinyl, 2-pyridinyl, 3-pyridinyl, 4-pyridinyl, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-furanyl, 3-furanyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalyl, 5-quinoxalyl, 6-quinoxalyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthrolin-2-yl, 1,7-phenanthrolin-3-yl, 1,7-phenanthrolin-4-yl, 1,7-phenanthrolin-5-yl, 1,7-phenanthrolin-6-yl, 1,7-phenanthrolin-8-yl, 1,7-phenanthrolin-9-yl, 1,7-phenanthrolin-10-yl, 1,8-phenanthrolin-2-yl, 1,8-phenanthrolin-3-yl, 1,8-phenanthrolin-4-yl, 1,8-phenanthrolin-5-yl, 1,8-phenanthrolin-6-yl, 1,8-phenanthrolin-7-yl, 1,8-phenanthrolin-9-yl, 1,8-phenanthrolin-10-yl, 1,9-phenanthrolin-2-yl, 1,9-phenanthrolin-3-yl, 1,9-phenanthrolin-4-yl, 1,9-phenanthrolin-5-yl, 1,9-phenanthrolin-6-yl, 1,9-phenanthrolin-7-yl, 1,9-phenanthrolin-8-yl, 1,9-phenanthrolin-10-yl, 1,10-phenanthrolin-2-yl, 1,10-phenanthrolin-3-yl, 1,10-phenanthrolin-4-yl, 1,10-phenanthrolin-5-yl, 2,9-phenanthrolin-1-yl, 2,9-phenanthrolin-3-yl, 2,9-phenanthrolin-4-yl, 2,9-phenanthrolin-5-yl, 2,9-phenanthrolin-6-yl, 2,9-phenanthrolin-7-yl, 2,9-phenanthrolin-8-yl, 2,9-phenanthrolin-10-yl, 2,8-phenanthrolin-1-yl, 2,8-phenanthrolin-3-yl, 2,8-phenanthrolin-4-yl, 2,8-phenanthrolin-5-yl, 2,8-phenanthrolin-6-yl, 2,8-phenanthrolin-7-yl, 2,8-phenanthrolin-9-yl, 2,8-phenanthrolin-10-yl, 2,7-phenanthrolin-1-yl, 2,7-phenanthrolin-3-yl, 2,7-phenanthrolin-4-yl, 2,7-phenanthrolin-5-yl, 2,7-phenanthrolin-6-yl, 2,7-phenanthrolin-8-yl, 2,7-phenanthrolin-9-yl, 2,7-phenanthrolin-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, and 4-tert-butyl-3-indolyl.

Preferably, the ester group having 2 to 20 carbon atoms is any one of methyl ester group, ethyl ester group, propyl ester group, isopropyl ester group, n-butyl ester group, sec-butyl ester group, isobutyl ester group, n-pentyl ester group, n-hexyl ester group, n-heptyl ester group, and n-octyl ester group.

Figure 2:
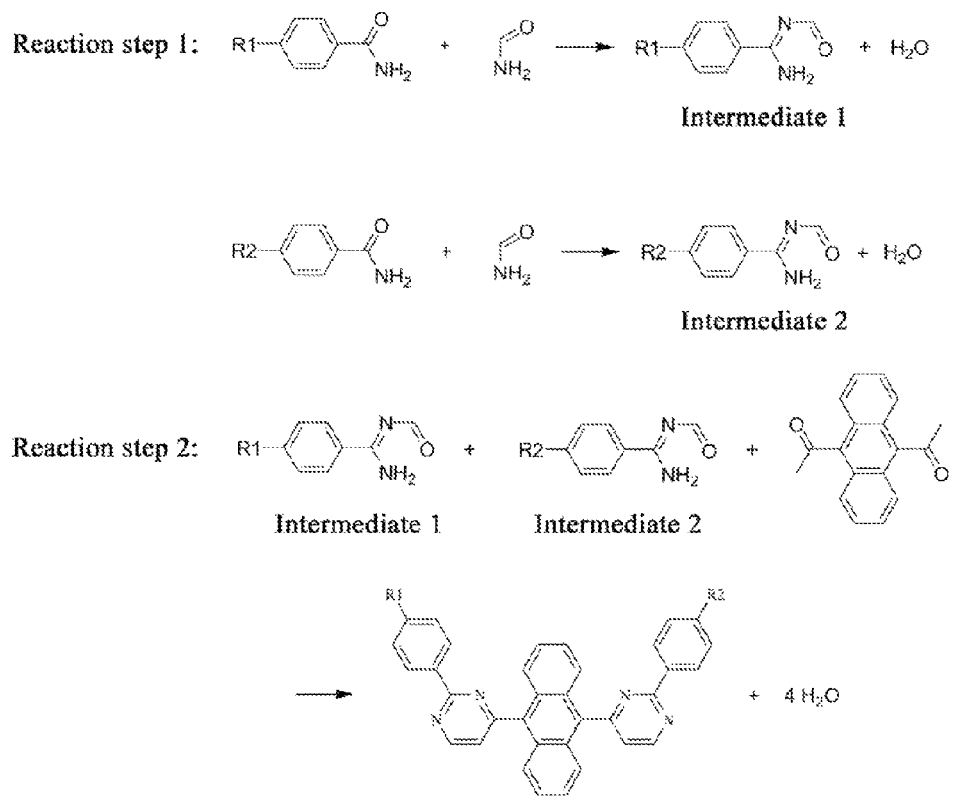
FIGS. 2 and 3 are flow diagrams illustrating the process for preparing the 9,10-bis[2-(p-substituted phenyl)pyrimidin-4-yl] anthracene compounds according to the present invention, wherein FIG. 2 relates to the compounds in which R1 and R2 are different, and FIG. 3 relates to the compounds in which R1 and R2 are the same (both represented by R).
Figure 3:
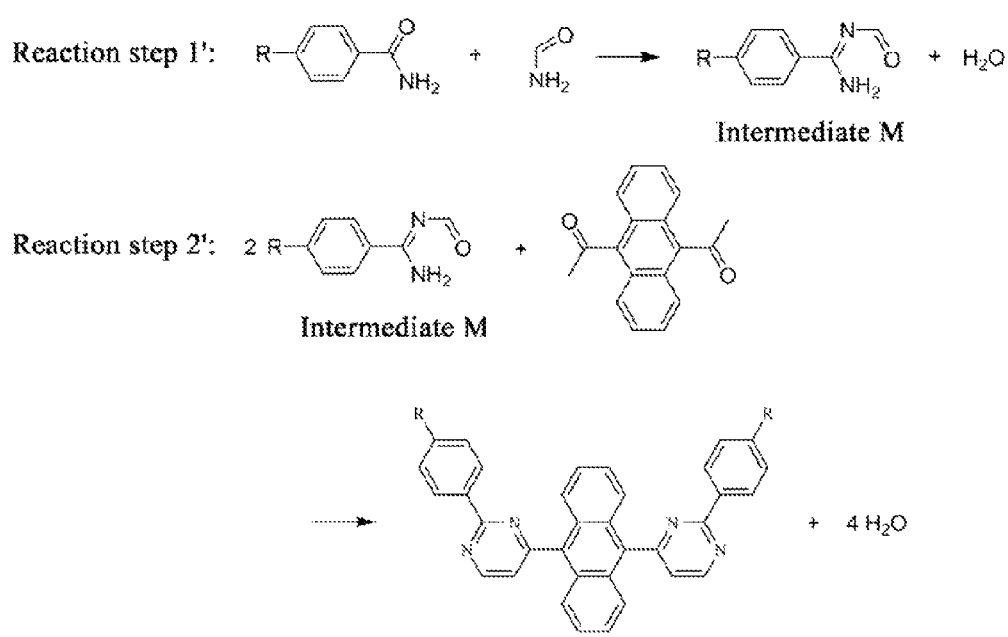

The present invention also provides a method of preparing the 9,10-bis[2-(p-substituted phenyl)pyrimidin-4-yl] anthracene compound represented by the aforesaid formula, comprising the following steps: reacting p-substituted benzamide with formamide to produce an intermediate; and reacting 9,10-diacetylanthracene with the intermediate to produce said 9,10-bis[2-(p-substituted phenyl)pyrimidin-4-yl] anthracene compound (as shown in FIGS. 2 and 3). More particularly, when R1 and R2 in the above formula are different, said method comprises the following steps (as shown in FIG. 2):

Reaction step 1: reacting p-R1-benzamide or p-R2-benzamide with formamide respectively to produce intermediate 1 or 2, as shown below:

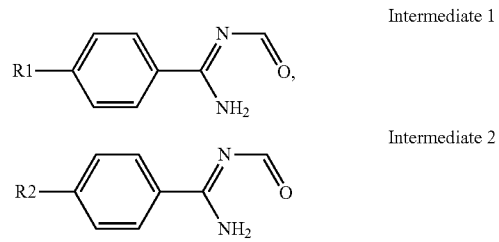

wherein R1 and R2 are defined as above, and R1 and R2 are different; and

Reaction step 2: reacting 9,10-diacetylanthracene with the intermediates 1 and 2 to produce said 9,10-bis[2-(p-substituted phenyl)pyrimidin-4-yl] anthracene compound.

When R1 and R2 in the above formula are the same, said method comprises the following steps (as shown in FIG. 3):

Reaction step 1': reacting p-R-benzamide with formamide to produce an intermediate M, as shown below:

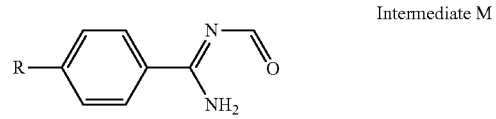

wherein R1 and R2 are defined as above, and R1=R2=R; and

Reaction step 2': reacting 9,10-diacetylanthracene with the intermediate M to produce said 9,10-bis[2-(p-substituted phenyl)pyrimidin-4-yl] anthracene compound.

In order to obtain the 9,10-bis[2-(p-substituted phenyl)pyrimidin-4-yl] anthracene compounds according to the present invention with a relatively high purity, the method preferably further comprises the step of separating and purifying the raw product of Reaction step 2 or 2'.

Preferably, in Reaction step 1 or 1', the mole ratio of the p-R1-benzamide, p-R2-benzamide or p-R-benzamide to formamide is 1:(1-1.5), respectively; reaction temperature is in the range of 50 to 150° C., and reaction time is in the range of 2 to 24 h.

Preferably, in Reaction step 2 or 2', the mole ratio of 9,10-diacetylanthracene to the intermediates 1 and 2 is 1:(1-1.5):(1-1.5), or the mole ratio of 9,10-diacetylanthracene to the intermediate M is 1:(2-3); reaction temperature is in the range of 50 to 150° C., and reaction time is in the range of 2 to 24 h.

Preferably, the separating and purifying step comprises:
acidifying the raw product and then extracting to obtain a first extract liquor;
alkalifying the first extract liquor and then extracting to obtain a second extract liquor; and separating the second extract liquor by a chromatographic column to obtain a pure 9,10-bis[2-(p-substituted phenyl)pyrimidin-4-yl] anthracene compound. Herein, "pure 9,10-bis[2-(p-substituted phenyl)pyrimidin-4-yl] anthracene compound" means that the compound has a purity of at least 90%, preferably at least 95%, more preferably at least 99% or even higher.

Extracting agents used in the separating and purifying step are common organic extraction agents, for example, ethyl ether, acetone, etc. The acidification is to adjust the pH below or equal to 6, preferably below or equal to 5, more preferably below or equal to 4 or even less, using HCl, $H_2SO_4$, or other acidic pH adjusting agents known in the art. The alkalization is to adjust the pH above or equal to 8, preferably above or equal to 9, more preferably above or equal to 10 or even higher, using a solution of alkali metal hydroxide (for example, NaOH or KOH solution), or other basic pH adjusting agents known in the art.

EXAMPLES

The following examples further illustrate the invention, but are not to be construed as limiting the invention thereto.

Example 1

This example provides a 9-(2-phenylpyrimidin-4-yl)-10-(2-p-carboxylphenyl pyrimidin-4-yl)anthracene compound and the preparation method thereof. The compound of the example has the formula shown in FIG. 1, wherein R1 is hydrogen, and R2 is carboxyl. Said compound was prepared by the following process (the flow diagram of the process is shown in FIG. 2):

1) Reaction Steps

Step 1-1: Preparation of Intermediate 1

A 100 mL three-neck flask, equipped with a magnetic stirrer and a condenser pipe having a dry filter, was put into an oil bath with a heating unit. 0.5 mol of benzamide (analytic reagent (AR), Peking Chemical Plant) and 0.5 mol of formamide (AR, Peking Chemical Plant) were added into the flask in sequence. After stirred well at room temperature, the mixture was heated to 100° C. for 5 h. The resultant product was slowly cooled to room temperature with stirring, and then was purified by recrystallization to obtain Intermediate 1. The mass-to-charge ratio of the Intermediate 1 was measured by a mass spectrometer (HP 1100LC-MSD), and the elemental analysis was performed on a Vario EL element analyzer (manufactured by Elementar Co., Germany). It has been determined by the analysis that the obtained Intermediate 1 is N'-formyl benzamidine, i.e. the Intermediate 1 shown in FIG. 2 wherein R1 is hydrogen. The data of mass spectra and elemental analysis thereof are as follows:

m/z: 148.06 (100.0%), 149.07 (8.8%);
Elemental Analysis: C, 64.85; H, 5.44; N, 18.91; O, 10.80.

Step 1-2: Preparation of Intermediate 2

A 100 mL three-neck flask, equipped with a magnetic stirrer and a condenser pipe having a dry filter, was put in an oil bath with a heating unit. 0.5 mol of p-carboxyl benzamide (AR, Sinopharm Chemical Reagent Co., Ltd; the reagents used in the following examples were all obtained from this company, unless indicated otherwise) was added into the flask, followed by addition of 0.5 mol of formamide (AR, Peking Chemical Plant). After stirred well at room temperature, the mixture was heated to 100° C. for 5 h, and then the reaction system was slowly cooled to room temperature with stirring to obtain Intermediate 2. By analysis as step 1-1, it has been determined that the Intermediate 2 is N'-formyl-p-carboxyl benzamidine, i.e. the Intermediate 2 shown in FIG. 2 wherein R2 is carboxyl. The data of mass spectra and elemental analysis thereof are as follows:

m/z: 192.05 (100.0%), 193.06 (9.9%), 194.06 (1.1%);
Elemental Analysis: C, 56.25; H, 4.20; N, 14.58; O, 24.98.

Step 2

Preparation of 9-(2-phenylpyrimidin-4-yl)-10-(2-p-carboxylphenylpyrimidin-4-yl)anthracene The Intermediate 1 obtained in step 1-1 was added into the Intermediate 2 obtained in step 1-2 at room temperature, and stirred well. Then, with stirring, 0.5 mol 9,10-biacetyl anthracene was added into the mixture and heated to 120° C. for 5 h to give a raw product of 9-(2-phenylpyrimidin-4-yl)-10-(2-p-carboxylphenyl pyrimidin-4-yl)anthracene.

2) Separation and Purification Steps

Acidification treatment: the pH of the raw product was adjusted to be acidic (pH=5.0) by adding concentrated HCl (12 mol/L) with stirring at 120° C. (in an oil bath), and the stirring and heating was kept for 2 h. Then, the acidified product was extracted by 20 mL absolute ethyl ether, and the ether layer was collected as a first extract liquor. The first extract liquor was poured into a beaker, and heated and stirred well.

Alkalinization treatment: the pH of the first extract liquor was adjusted to be basic (pH=10.0) by adding NaOH solution (3 mol/L). Then, the alkalified first extract liquor was extracted by 20 mL absolute ethyl ether, and the ether layer was collected as a second extract liquor.

The second extract liquor was purified by a column separation process, with absolute ethyl ether being used as an eluent, and silica gel (60-100 mesh, AR, Peking Chemical Plant) being used as a stationary phase. The collected eluate was concentrated by rotary evaporation and then dried under vacuum to obtain the compound 9-(2-phenylpyrimidin-4-yl)-10-(2-p-carboxylphenylpyrimidin-4-yl)anthracene (0.2 mol, purity >99%, faint yellow powder).

The mass-to-charge ratio of the compound produced by this example was measured by the mass spectrometer, and the elemental analysis was performed on the Vario EL element analyzer. The measurement results are as follows:

m/z: 530.17 (100.0%), 531.18 (38.2%), 532.18 (7.5%), 531.17 (1.5%), 533.18 (1.1%);
Elemental Analysis: C, 79.23; H, 4.18; N, 10.56; O, 6.03.

The compound produced by this example was used for preparation of the light-emitting layers in organic electroluminescent devices, according to the common fabrication method of making light emitting diodes and techniques known in the art of organic electroluminescent devices, and a device with the following structure was obtained:

ITO/CuPc (15 nm)/NPB (75 nm)/light-emitting layer (30 nm)/Alq3 (35 nm)/LiF (0.5 nm)/MgAg (10:1, 100 nm).

The device was tested by PR680 (manufactured by PhotoResearch Co., U.S.), and its performance parameters are as follows:

Chromaticity coordinates: (X=0.15, Y=0.22);
Turn-on voltage: 4.5 V;
Max luminance: 40020 cd/m2 (12V);
Luminous efficiency: 10 cd/A.

It can be seen that the luminous efficiency is significantly improved, as compared with that of the devices according to the prior art (about 5 cd/A).

Example 2

This example provides a 9,10-bis(2-p-carboxylphenylpyrimidin-4-yl)anthracene compound and the preparation method thereof. The compound of the example has the formula shown in FIG. 1, wherein R1 and R2 are the same, and both of them are carboxyl. Said compound was prepared by the following process (the flow diagram of the process is shown in FIG. 3):

1) Reaction Steps

Step 1: Preparation of Intermediate M

A three-neck flask, equipped with a magnetic stirrer and a condenser pipe having a dry filter, was put into an oil bath with a heating unit. 1.1 mol of p-carboxyl benzamide (AR, Sinopharm Chemical Reagent Co., Ltd.) was added into the flask, followed by addition of 1.5 mol formamide (AR, Peking Chemical Plant). After stirred well at room temperature, the mixture was heated to 120° C. for 2 h to obtain Intermediate M. By analysis as Example 1, it has been determined that the Intermediate M is N'-formyl-p-carboxyl benzamidine, i.e. the Intermediate M shown in FIG. 3 wherein R is carboxyl.

Step 2: Preparation of 9,10-bis(2-p-carboxylphenylpyrimidin-4-yl)anthracene

With stirring, 0.5 mol 9,10-diacetylanthracene was added into the Intermediate M obtained in Step 1 and heated to 120° C. for 2 h to give a raw product of the title compound.

2) Separation and Purification Steps

Acidification treatment: the pH of the raw product was adjusted to be acidic (pH=5.5) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=9.0) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-p-carboxylphenylpyrimidin-4-yl)anthracene (0.25 mol, purity >99%). As described in Example 1, the compound produced by this example was confirmed by mass spectrometry and elemental analysis. The measurement results are as follows:

m/z: 574.16 (100.0%), 575.17 (39.3%), 576.17 (8.4%), 575.16 (1.5%), 577.17 (1.3%);

Elemental Analysis: C, 75.25; H, 3.86; N, 9.75; O, 11.14.

The compound 9,10-bis(2-p-carboxylphenylpyrimidin-4-yl)anthracene produced by this example was used for preparation of the light-emitting layers in organic electroluminescent devices, and a device with the following structure was obtained:

ITO/CuPc (15 nm)/NPB (75 nm)/light-emitting layer (30 nm)/Alq3 (35 nm)/LiF (0.5 nm)/MgAg (10:1, 100 nm).

The device was tested by PR680, and its performance parameters are as follows:

Chromaticity coordinates: (X=0.15, Y=0.25)
Turn-on voltage: 4.3 V;
Max luminance: 45000 cd/m2 (12 V);
Luminous efficiency: 12 cd/A.

It can be seen that the luminous efficiency is significantly improved, as compared with that of the devices according to the prior art (about 5 cd/A).

Example 3

This example provides a 9,10-bis(2-(p-difluoromethylphenyl)pyrimidin-4-yl)anthracene compound and the preparation method thereof. The compound of the example has the formula shown in FIG. 1, wherein R1 and R2 are the same, and both of them are 1,1-difluoromethyl. Said compound was prepared by the following process (the flow diagram of the process is shown in FIG. 3):

1) Reaction Steps

Step 1: Preparation of Intermediate M

Intermediate M was prepared as described in Example 2, except that 1.2 mol of p-difluoromethyl benzamide and 1.3 mol of formamide were used as raw materials and the mixture thereof was heated to 110° C. for 9 h to give N'-formyl-p-difluoromethyl benzamidine, i.e. the Intermediate M shown in FIG. 3 wherein R is 1,1-difluoromethyl.

Step 2: Preparation of 9,10-bis(2-(p-difluoromethylphenyl)pyrimidin-4-yl)anthracene With stirring, 0.5 mol 9,10-diacetylanthracene was added into the Intermediate M obtained in Step 1 and heated to 110° C. for 9 h to give a raw product of 9,10-bis(2-(p-difluoromethylphenyl)pyrimidin-4-yl)anthracene.

2) Separation and Purification Steps

Acidification treatment: the pH of the raw product was adjusted to be acidic (pH=5.5) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=10.5) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-(p-difluoromethylphenyl)pyrimidin-4-yl)anthracene (0.28 mol, purity >99%). As described in Example 2, the compound produced by this example was confirmed by mass spectrometry and elemental analysis. The measurement results are as follows:

m/z: 606.26 (100.0%), 607.26 (44.7%), 608.27 (9.3%), 609.27 (1.3%);

Elemental Analysis: C, 79.19; H, 5.32; F, 6.26; N, 9.23.

The compound 9,10-bis(2-(p-difluoromethylphenyl)pyrimidin-4-yl)anthracene produced by this example was used for preparation of the light-emitting layers in organic electroluminescent devices, and a device with the following structure was obtained:

ITO/CuPc (15 nm)/NPB (75 nm)/light-emitting layer (30 nm)/Alq3 (35 nm)/LiF (0.5 nm)/MgAg (10:1, 100 nm).

The device was tested by PR680, and its performance parameters are as follows:

Chromaticity coordinates: (X=0.15, Y=0.25);
Turn-on voltage: 4.3 V;
Max luminance: 50000 cd/m2 (12 V);
Luminous efficiency: 14 cd/A.

It can be seen that the luminous efficiency is significantly improved, as compared with that of the devices according to the prior art (about 5 cd/A).

Example 4

This example provides a 9,10-bis(2-p-cyanophenylpyrimidin-4-yl)anthracene compound and the preparation method thereof. The compound of the example has the formula shown in FIG. 1, wherein R1 and R2 are the same, and both of them are cyano. Said compound was prepared by the following process (the flow diagram of the process is shown in FIG. 3):

1) Reaction Steps

Step 1: Preparation of Intermediate M

Intermediate M was prepared as described in Example 2, except that 1.3 mol of p-cyano benzamide and 1.4 mol of formamide were used as raw materials and the mixture thereof was heated to 150° C. for 6 h to give N'-formyl-p-cyano benzamidine, i.e. the Intermediate M shown in FIG. 3 wherein R is cyano.

Step 2: Preparation of
9,10-bis(2-p-cyanophenylpyrimidin-4-yl)anthracene

With stirring, 0.5 mol 9,10-diacetylanthracene was added into the Intermediate M obtained in Step 1 and heated to 150° C. for 6 h to give a raw product of 9,10-bis(2-(p-dicyanophenyl)pyrimidin-4-yl)anthracene.

2) Separation and Purification Steps

Acidification treatment: the pH of the raw product was adjusted to be acidic (pH=4.5) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=11.0) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-(p-cyanophenyl)pyrimidin-4-yl)anthracene (0.30 mol, purity >99%). As described in Example 2, the compound produced by this example was confirmed by mass spectrometry and elemental analysis. The measurement results are as follows:

m/z: 536.17 (100.0%), 537.18 (39.2%), 538.18 (8.3%), 537.17 (2.2%);

Elemental Analysis: C, 80.58; H, 3.76; N, 15.66.

Optionally, the compound 9,10-bis(2-p-cyanophenylpyrimidin-4-yl)anthracene produced by this example was used for preparation of the light-emitting layers in organic electroluminescent devices so as to obtain an organic electroluminescent device.

Example 5

This example provides a 9,10-bis(2-p-nitrophenylpyrimidin-4-yl)anthracene compound and the preparation method thereof. The compound of the example has the formula shown in FIG. 1, wherein R1 and R2 are the same, and both of them are nitro. Said compound was prepared by the following process (the flow diagram of the process is shown in FIG. 3):

1) Reaction Steps

Step 1: Preparation of Intermediate M

Intermediate M was prepared as described in Example 2, except that 1.1 mol of p-nitrobenzamide and 1.5 mol of formamide were used as raw materials and the mixture thereof was heated to 70° C. for 15 h to give N'-formyl-p-nitro benzamidine, i.e. the Intermediate M shown in FIG. 3 wherein R is nitro.

Step 2: Preparation of
9,10-bis(2-p-nitrophenylpyrimidin-4-yl)anthracene

With stirring, 0.5 mol 9,10-diacetylanthracene was added into the Intermediate M obtained in Step 1 and heated to 70° C. for 15 h to give a raw product of 9,10-bis(2-(p-nitrophenylpyrimidin-4-yl)anthracene.

2) Separation and Purification Steps

Acidification treatment: the pH of the raw product was adjusted to be acidic (pH=4.2) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=12.4) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis (2-p-nitrophenylpyrimidin-4-yl)anthracene (0.27 mol, purity >99%). As described in Example 2, the compound produced by this example was confirmed by mass spectrometry and elemental analysis. The measurement results are as follows:

m/z: 576.15 (100.0%), 577.16 (37.2%), 578.16 (7.5%), 577.15 (2.2%), 579.16 (1.2%)

Elemental Analysis: C, 70.83; H, 3.50; N, 14.58; O, 11.10.

Optionally, the compound 9,10-bis(2-p-nitrophenylpyrimidin-4-yl)anthracene produced by this example was used for preparation of the light-emitting layers in organic electroluminescent devices so as to obtain an organic electroluminescent device.

Example 6

This example provides a 9,10-bis(2-p-methylphenylpyrimidin-4-yl)anthracene compound and the preparation method thereof. The compound of the example has the formula shown in FIG. 1, wherein R1 and R2 are the same, and both of them are methyl. Said compound was prepared by the following process (the flow diagram of the process is shown in FIG. 3):

1) Reaction Steps

Step 1: Preparation of Intermediate M

Intermediate M was prepared as described in Example 2, except that 1.1 mol of p-methyl benzamide and 1.5 mol of formamide were used as raw materials and the mixture thereof was heated to 60° C. for 7 h to give N'-formyl-p-methyl benzamidine, i.e. the Intermediate M shown in FIG. 3 wherein R is methyl.

Step 2: Preparation of 9,10-bis(2-p-methylphenylpyrimidin-4-yl)anthracene

With stirring, 0.5 mol 9,10-diacetylanthracene was added into the Intermediate M obtained in Step 1 and heated to 60° C. for 7 h to give a raw product of 9,10-bis(2-(p-methylphenylpyrimidin-4-yl)anthracene.

2) Separation and Purification Steps

Acidification treatment: the pH of the raw product was adjusted to be acidic (pH=3.3) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=8.6) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-p-methylphenylpyrimidin-4-yl)anthracene (0.32 mol, purity >99%). As described in Example 2, the compound produced by this example was confirmed by mass spectrometry and elemental analysis. The measurement results are as follows:

m/z: 514.22 (100.0%), 515.22 (39.2%), 516.22 (7.9%), 515.21 (1.5%)

Elemental Analysis: C, 84.02; H, 5.09; N, 10.89

Optionally, the compound 9,10-bis(2-p-methylphenylpyrimidin-4-yl)anthracene produced by this example was used for preparation of the light-emitting layers in organic electroluminescent devices so as to obtain an organic electroluminescent device.

Example 7

This example provides a 9,10-bis(2-p-tert-butylphenylpyrimidin-4-yl)anthracene compound and the preparation method thereof. The compound of the example has the formula shown in FIG. 1, wherein R1 and R2 are the same, and both of them are tert-butyl. Said compound was prepared by the following process (the flow diagram of the process is shown in FIG. 3):

1) Reaction Steps

Step 1: Preparation of Intermediate M

Intermediate M was prepared as described in Example 2, except that 1.2 mol of p-tert-butyl benzamide and 1.5 mol of formamide were used as raw materials and the mixture thereof was heated to 60° C. for 7 h to give N'-formyl-p-tert-butyl benzamidine, i.e. the Intermediate M shown in FIG. 3 wherein R is tert-butyl.

Step 2: Preparation of 9,10-bis(2-p-tert-butylphenylpyrimidin-4-yl)anthracene

With stirring, 0.5 mol 9,10-diacetylanthracene was added into the Intermediate M obtained in Step 1 and heated to 60° C. for 7 h to give a raw product of 9,10-bis(2-p-tert-butylphenylpyrimidin-4-yl)anthracene.

2) Separation and Purification Steps

Acidification treatment: the pH of the raw product was adjusted to be acidic (pH=5.6) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=10.8) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-(p-tert-butylphenylpyrimidin-4-yl)anthracene (0.24 mol, purity >99%). As described in Example 2, the compound produced by this example was confirmed by mass spectrometry and elemental analysis. The measurement results are as follows:

m/z: 598.31 (100.0%), 599.31 (46.9%), 600.32 (10.3%), 601.32 (1.5%)

Elemental Analysis: C, 84.25; H, 6.40; N, 9.36.

Optionally, the compound 9,10-bis(2-p-tert-butylphenylpyrimidin-4-yl)anthracene produced by this example was used for preparation of the light-emitting layers in organic electroluminescent devices so as to obtain an organic electroluminescent device.

Example 8

This example provides a 9,10-bis(2-p-hydroxymethylphenylpyrimidin-4-yl)anthracene compound and the preparation method thereof. The compound of the example has the formula shown in FIG. 1, wherein R1 and R2 are the same, and both of them are hydroxymethyl. Said compound was prepared by the following process (the flow diagram of the process is shown in FIG. 3):

1) Reaction Steps

Step 1: Preparation of Intermediate M

Intermediate M was prepared as described in Example 2, except that 1.3 mol of p-hydroxymethyl benzamide and 1.3 mol of formamide were used as raw materials and the mixture thereof was heated to 90° C. for 3 h to give N'-formyl-p-hydroxymethyl benzamidine, i.e. the Intermediate M shown in FIG. 3 wherein R is hydroxymethyl.

Step 2: Preparation of 9,10-bis(2-p-hydroxymethylphenylpyrimidin-4-yl)anthracene With stirring, 0.5 mol 9,10-diacetylanthracene was added into the Intermediate M obtained in Step 1 and heated to 90° C. for 3 h to give a raw product of 9,10-bis(2-(p-hydroxymethylphenylpyrimidin-4-yl)anthracene.

2) Separation and Purification Steps

Acidification treatment: the pH of the raw product was adjusted to be acidic (pH=3.5) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=11.4) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis (2-(p-hydroxymethylphenylpyrimidin-4-yl)anthracene (0.28 mol, purity >99%). As described in Example 2, the compound produced by this example was confirmed by mass spectrometry and elemental analysis. The measurement results are as follows:

m/z: 546.21 (100.0%), 547.21 (39.3%), 548.21 (8.4%), 547.20 (1.5%)

Elemental Analysis: C, 79.10; H, 4.79; N, 10.25; O, 5.85

Optionally, the compound 9,10-bis(2-p-hydroxymethylphenyl pyrimidin-4-yl)anthracene produced by this example was used for preparation of the light-emitting layers in organic electroluminescent devices so as to obtain an organic electroluminescent device.

Example 9

This example provides a 9,10-bis(2-(p-(3-aminopropyl) phenyl)pyrimidin-4-yl)anthracene compound and the preparation method thereof. The compound of the example has the formula shown in FIG. 1, wherein R1 and R2 are the same, and both of them are 3-amimopropyl. Said compound was prepared by the following process (the flow diagram of the process is shown in FIG. 3):

1) Reaction Steps

Step 1: Preparation of Intermediate M

Intermediate M was prepared as described in Example 2, except that 1.3 mol of p-(3-aminopropyl)benzamide and 1.4 mol of formamide were used as raw materials and the mixture thereof was heated to 100° C. for 3 h to give N'-formyl-p-(3-aminopropyl)benzamidine, i.e. the Intermediate M shown in FIG. 3 wherein R is 3-aminopropyl.

Step 2: Preparation of 9,10-bis(2-(p-(3-aminopropyl)phenyl)pyrimidin-4-yl)anthracene With stirring, 0.5 mol 9,10-diacetylanthracene was added into the Intermediate M obtained in Step 1 and heated to 100° C. for 3 h to give a raw product of 9,10-bis(2-(p-(3-aminopropyl)phenyl)pyrimidin-4-yl)anthracene.

2) Separation and Purification Steps

Acidification treatment: the pH of the raw product was adjusted to be acidic (pH=2.5) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=12.0) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis (2-(p-(3-aminopropyl)phenyl)pyrimidin-4-yl)anthracene (0.35 mol, purity >99%). As described in Example 2, the compound produced by this example was confirmed by mass spectrometry and elemental analysis. The measurement results are as follows:

m/z: 600.30 (100.0%), 601.30 (45.5%), 602.31 (9.3%), 603.31 (1.3%)

Elemental Analysis: C, 79.97; H, 6.04; N, 13.99

Optionally, the compound 9,10-bis(2-(p-(3-aminopropyl) phenyl)pyrimidin-4-yl)anthracene produced by this example was used for preparation of the light-emitting layers in organic electroluminescent devices so as to obtain an organic electroluminescent device.

Example 10

This example provides a 9,10-bis(2-(p-cyclopropylphenyl)pyrimidin-4-yl)anthracene compound and the preparation method thereof. The compound of the example has the formula shown in FIG. 1, wherein R1 and R2 are the same, and both of them are cyclopropyl. Said compound was prepared by the following process (the flow diagram of the process is shown in FIG. 3):

1) Reaction Steps

Step 1: Preparation of Intermediate M

Intermediate M was prepared as described in Example 2, except that 1.2 mol of p-cyclopropyl benzamide and 1.4 mol of formamide were used as raw materials and the mixture thereof was heated to 120° C. for 13 h to give N'-formyl-p-cyclopropyl benzamidine, i.e. the Intermediate M shown in FIG. 13 wherein R is cyclopropyl.

Step 2: Preparation of 9,10-bis(2-(p-cyclopropyl-phenyl)pyrimidin-4-yl)anthracene With stirring, 0.5 mol 9,10-diacetylanthracene was added into the Intermediate M obtained in Step 1 and heated to 120° C. for 13 h to give a raw product of 9,10-bis(2-(p-cyclopropylphenyl)pyrimidin-4-yl)anthracene.

2) Separation and Purification Steps

Acidification treatment: the pH of the raw product was adjusted to be acidic (pH=2.5) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=13.0) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-(p-cyclopropylphenyl)pyrimidin-4-yl)anthracene (0.27 mol, purity >99%). As described in Example 2, the compound produced by this example was confirmed by mass spectrometry and elemental analysis. The measurement results are as follows:

m/z: 566.25 (100.0%), 567.25 (43.6%), 568.25 (9.8%), 567.24 (1.5%), 569.26 (1.3%)

Elemental Analysis: C, 84.78; H, 5.34; N, 9.89

Optionally, the compound 9,10-bis(2-(p-cyclopropylphenyl)pyrimidin-4-yl)anthracene produced by this example was used for preparation of the light-emitting layers in organic electroluminescent devices so as to obtain an organic electroluminescent device.

Example 11

This example provides a 9,10-bis(2-(p-(3-nitropropoxy)phenyl)pyrimidin-4-yl)anthracene compound and the preparation method thereof. The compound of the example has the formula shown in FIG. 1, wherein R1 and R2 are the same, and both of them are alkoxyl (in which the alkyl is 3-nitropropyl). Said compound was prepared by the following process (the flow diagram of the process is shown in FIG. 3):

1) Reaction Steps

Step 1: Preparation of Intermediate M

Intermediate M was prepared as described in Example 2, except that 1.5 mol of p-(3-nitropropoxy)benzamide and 1.5 mol of formamide were used as raw materials and the mixture thereof was heated to 150° C. for 2 h to give N'-formyl-p-(3-nitropropoxy)benzamidine, i.e. the Intermediate M shown in FIG. 3 wherein R is alkoxyl (in which the alkyl is 3-nitropropyl).

Step 2: Preparation of 9,10-bis(2-(p-(3-nitropropoxy)phenyl)pyrimidin-4-yl)anthracene With stirring, 0.5 mol 9,10-diacetylanthracene was added into the Intermediate M obtained in Step 1 and heated to 150° C. for 2 h to give a raw product of 9,10-bis(2-(p-(3-nitropropoxy)phenyl)pyrimidin-4-yl)anthracene.

2) Separation and Purification Steps

Acidification treatment: the pH of the raw product was adjusted to be acidic (pH=5.5) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=10.0) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-(p-(3-nitropropoxy)phenyl)pyrimidin-4-yl)anthracene (0.33 mol, purity >99%). As described in Example 2, the compound produced by this example was confirmed by mass spectrometry and elemental analysis. The measurement results are as follows:

m/z: 632.22 (100.0%), 633.22 (41.6%), 634.22 (10.0%), 633.21 (2.2%), 635.23 (1.1%)

Elemental Analysis: C, 72.14; H, 4.46; N, 13.28; O, 10.12

Optionally, the compound 9,10-bis(2-(p-(3-nitropropoxy)phenyl)pyrimidin-4-yl)anthracene produced by this example was used for preparation of the light-emitting layers in organic electroluminescent devices so as to obtain an organic electroluminescent device.

Example 12

This example provides a 9,10-bis(2-p-(1,3-dinitropropoxy)phenylpyrimidin-4-yl)anthracene compound and the preparation method thereof. The compound of the example has the formula shown in FIG. 1, wherein R1 and R2 are the same, and both of them are alkoxyl (in which the alkyl is 1,3-dinitropropyl). Said compound was prepared by the following process (the flow diagram of the process is shown in FIG. 3):

1) Reaction Steps

Step 1: Preparation of Intermediate M

Intermediate M was prepared as described in Example 2, except that 1.2 mol of p-(1,3-dinitropropoxy)benzamide and 1.2 mol of formamide were used as raw materials and the mixture thereof was heated to 140° C. for 15 h to give N'-formyl-p-(1,3-dinitropropoxy)benzamidine, i.e. the Intermediate M shown in FIG. 1.3 wherein R is alkoxyl (in which the alkyl is 1,3-dinitropropyl).

Step 2: Preparation of 9,10-bis(2-p-(1,3-dinitropropoxy)phenylpyrimidin-4-yl)anthracene With stirring, 0.5 mol 9,10-diacetylanthracene was added into the Intermediate M obtained in Step 1 and heated to 140° C. for 12 h to give a raw product of 9,10-bis(2-p-(1,3-dinitropropoxy)phenylpyrimidin-4-yl)anthracene.

2) Separation and Purification Steps

Acidification treatment: the pH of the raw product was adjusted to be acidic (pH=6.0) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=9.5) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-p-(1,3-dinitropropoxy)phenylpyrimidin-4-yl)anthracene (0.24 mol, purity >99%). As described in Example 2, the compound produced by this example was confirmed by mass spectrometry and elemental analysis. The measurement results are as follows:

m/z: 782.21 (100.0%), 783.21 (46.9%), 784.22 (9.4%), 784.21 (3.4%), 785.22 (2.2%)

Elemental Analysis: C, 61.38; H, 3.86; N, 14.32; O, 20.44

Optionally, the compound 9,10-bis(2-p-(1,3-dinitropropoxy)phenylpyrimidin-4-yl)anthracene produced by this example was used for preparation of the light-emitting layers in organic electroluminescent devices so as to obtain an organic electroluminescent device.

Example 13

This example provides a 9,10-bis(2-(4-biphenyl)pyrimidin-4-yl)anthracene compound and the preparation method thereof. The compound of the example has the formula shown in FIG. 1, wherein R1 and R2 are the same, and both of them are phenyl. Said compound was prepared by the following process (the flow diagram of the process is shown in FIG. 3):

1) Reaction Steps

Step 1: Preparation of Intermediate M

Intermediate M was prepared as described in Example 2, except that 1.5 mol of 4-biphenyl formamide and 1.4 mol of formamide were used as raw materials and the mixture thereof was heated to 60° C. for 22 h to give N'-formyl-4-biphenyl formamidine, i.e. the Intermediate M shown in FIG. 3 wherein R is phenyl.

Step 2: Preparation of 9,10-bis(2-(4-biphenyl)pyrimidin-4-yl)anthracene

With stirring, 0.5 mol 9,10-diacetylanthracene was added into the Intermediate M obtained in Step 1 and heated to 60° C. for 22 h to give a raw product of 9,10-bis(2-(4-biphenyl)pyrimidin-4-yl)anthracene.

2) Separation and Purification Steps

Acidification treatment: the pH of the raw product was adjusted to be acidic (pH=3.5) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=11.5) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-(4-biphenyl)pyrimidin-4-yl)anthracene (0.31 mol, purity >99%). As described in Example 2, the compound produced by this example was confirmed by mass spectrometry and elemental analysis. The measurement results are as follows:

m/z: 638.25 (100.0%), 639.25 (50.1%), 640.25 (12.8%), 641.26 (2.0%), 639.24 (1.5%)

Elemental Analysis: C, 86.49; H, 4.73; N, 8.77

Optionally, the compound 9,10-bis(2-(4-biphenyl)pyrimidin-4-yl)anthracene produced by this example was used for preparation of the light-emitting layers in organic electroluminescent devices so as to obtain an organic electroluminescent device.

Example 14

This example provides a 9,10-bis(2-(p-phenoxyphenyl)pyrimidin-4-yl)anthracene compound and the preparation method thereof. The compound of the example has the formula shown in FIG. 1, wherein R1 and R2 are the same, and both of them are phenoxy. Said compound was prepared by the following process (the flow diagram of the process is shown in FIG. 3):

1) Reaction Steps

Step 1: Preparation of Intermediate M

Intermediate M was prepared as described in Example 2, except that 1.5 mol of p-phenoxy benzamide and 1.2 mol of formamide were used as raw materials and the mixture thereof was heated to 150° C. for 21 h to give N'-formyl-p-phenoxy benzamidine, i.e. the Intermediate M shown in FIG. 3 wherein R is aryloxy (in which the aryl is phenyl).

Step 2: Preparation of 9,10-bis(2-(p-phenoxyphenyl)pyrimidin-4-yl)anthracene

With stirring, 0.5 mol 9,10-diacetylanthracene was added into the Intermediate M obtained in Step 1 and heated to 150° C. for 15 h to give a raw product of 9,10-bis(2-(p-phenoxyphenyl)pyrimidin-4-yl)anthracene.

2) Separation and Purification Steps

Acidification treatment: the pH of the raw product was adjusted to be acidic (pH=3.5) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=11.4) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-(p-phenoxyphenyl)pyrimidin-4-yl)anthracene (0.26 mol, purity >99%). As described in Example 2, the compound produced by this example was confirmed by mass spectrometry and elemental analysis. The measurement results are as follows:

m/z: 670.24 (100.0%), 671.24 (50.2%), 672.24 (13.3%), 673.25 (2.0%), 671.23 (1.5%)

Elemental Analysis: C, 82.37; H, 4.51; N, 8.35; O, 4.77

Optionally, the compound 9,10-bis(2-(p-phenoxyphenyl)pyrimidin-4-yl)anthracene produced by this example was used for preparation of the light-emitting layers in organic electroluminescent devices so as to obtain an organic electroluminescent device.

Example 15

This example provides a 9,10-bis(2-(p-methoxycarbonylphenyl)pyrimidin-4-yl)anthracene compound and the preparation method thereof. The compound of the example has the formula shown in FIG. 1, wherein R1 and R2 are the same, and both of them are methoxycarbonyl (i.e., methyl ester group). Said compound was prepared by the following process (the flow diagram of the process is shown in FIG. 3):

1) Reaction Steps

Step 1: Preparation of Intermediate M

Intermediate M was prepared as described in Example 2, except that 1.2 mol of p-methoxycarbonyl benzamide and 1.5 mol of formamide were used as raw materials and the mixture thereof was heated to 150° C. for 6 h to give N'-formyl-p-methoxycarbonyl benzamidine, i.e. the Intermediate M shown in FIG. 3 wherein R is methoxycarbonyl (i.e., methyl ester group).

Step 2: Preparation of 9,10-bis(2-(p-methoxycarbonylphenyl)pyrimidin-4-yl)anthracene With stirring, 0.5 mol 9,10-diacetylanthracene was added into the Intermediate M obtained in Step 1 and heated to 150° C. for 5 h to give a raw product of 9,10-bis(2-(p-methoxycarbonylphenyl)pyrimidin-4-yl)anthracene.

2) Separation and Purification Steps

Acidification treatment: the pH of the raw product was adjusted to be acidic (pH=5.5) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=10.5) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-(p-methoxycarbonylphenyl)pyrimidin-4-yl)anthracene (0.27 mol, purity >99%). As described in Example 2, the compound produced by this example was confirmed by mass spectrometry and elemental analysis. The measurement results are as follows:

m/z: 602.20 (100.0%), 603.20 (41.6%), 604.20 (9.7%), 603.19 (1.5%), 605.21 (1.1%)

Elemental Analysis: C, 75.73; H, 4.35; N, 9.30; O, 10.62

Optionally, the compound 9,10-bis(2-(p-methoxycarbonylphenyl)pyrimidin-4-yl)anthracene produced by this example was used for preparation of the light-emitting layers in organic electroluminescent devices so as to obtain an organic electroluminescent device.

Example 16

This example provides a 9,10-bis(2-(p-isobutoxycarbonylphenyl)pyrimidin-4-yl)anthracene compound and the preparation method thereof. The compound of the example has the formula shown in FIG. 1, wherein R1 and R2 are the same, and both of them are isobutoxycarbonyl (i.e., isobutyl ester group). Said compound was prepared by the following process (the flow diagram of the process is shown in FIG. 3):

1) Reaction Steps

Step 1: Preparation of Intermediate M

Intermediate M was prepared as described in Example 2, except that 1.5 mol of p-isobutoxycarbonyl benzamide and 1.2 mol of formamide were used as raw materials and the mixture thereof was heated to 140° C. for 10 h to give N'-formyl-p-isobutoxycarbonyl benzamidine, i.e. the Intermediate M shown in FIG. 3 wherein R is isobutoxycarbonyl (i.e., isobutyl ester group).

Step 2: Preparation of 9,10-bis(2-(p-isobutoxycarbonylphenyl)pyrimidin-4-yl)anthracene With stirring, 0.5 mol 9,10-diacetylanthracene was added into the Intermediate M obtained in Step 1 and heated to 140° C. for 8 h to give a raw product of 9,10-bis(2-(p-isobutoxycarbonylphenyl)pyrimidin-4-yl)anthracene.

2) Separation and Purification Steps

Acidification treatment: the pH of the raw product was adjusted to be acidic (pH=2.5) by adding concentrated HCl (12 mol/L) with stirring at 120° C. (in an oil bath), and the stirring and heating was kept for 2 h. Then, the acidified product was extracted by absolute ethyl ether, and the ether layer was collected as a first extract liquor. The first extract liquor was poured into a beaker, and heated and stirred well.

Alkalinization treatment: the pH of the first extract liquor was adjusted to be basic (pH=11.5) by adding NaOH solution (3 mol/L). Then, the alkalified first extract liquor was extracted by absolute ethyl ether, and the ether layer was collected as a second extract liquor.

The second extract liquor was purified by a column separation process, with absolute ethyl ether being used as an eluent, and silica gel being used as a stationary phase. The collected eluate was concentrated by rotary evaporation and then dried under vacuum to obtain the compound 9,10-bis(2-(p-isobutoxycarbonylphenyl)pyrimidin-4-yl)anthracene (0.29 mol, purity >99%). As described in Example 2, the compound produced by this example was confirmed by mass spectrometry and elemental analysis. The measurement results are as follows:

m/z: 686.29 (100.0%), 687.29 (49.2%), 688.30 (11.3%), 689.30 (2.1%), 688.29 (1.5%)

Elemental Analysis: C, 76.95; H, 5.58; N, 8.16; O, 9.32

Optionally, the compound 9,10-bis(2-(p-isobutoxycarbonylphenyl)pyrimidin-4-yl)anthracene produced by this example was used for preparation of the light-emitting layers in organic electroluminescent devices so as to obtain an organic electroluminescent device.

Although in some examples only one kind of benzamide having a para-substituent R (i.e. R1 and R2 in the above formula are the same) was used, it should be understood that Reaction Step 1 may also involve two kinds of benzamides individually having a para-substituent R (i.e. R1 and R2 in the above formula are different), as described in Example 1.

It is noted that in Examples 1-3 the structure and performance parameters of the organic electroluminescent devices are provided for illustration. Similarly, the 9,10-bis(2-(p-substituted phenyl)pyrimidin-4-yl)anthracene compounds prepared by other examples according to the present invention also can be used for preparation of the light-emitting layers in organic electroluminescent devices, and the results have verified that the luminous efficiency thereof is significantly improved (at least by 50%, and even 100% or more), as compared with that of the devices according to the prior art.

It should be understood that the pH adjusting agent (condensed HCl) used in the acidification treatment described above may also be selected from other acidic pH adjusting agents, such as H2SO4 or the like, and the pH adjusting agent (NaOH solution) used in the alkalinization treatment described above may also be selected from other basic pH adjusting agents, such as KOH or the like.

The 9,10-bis[2-(p-substituted phenyl)pyrimidin-4-yl]anthracene compounds according to the present invention can be used as blue-phosphorescent organic electroluminescent materials. Since such compounds per se have an ability to block holes, there is no need to arrange an HBL between the light-emitting layer and the ETL, and thus the evaporation chamber for deposition of the HBL is no longer needed in mass production of full color display panels of organic electroluminescent display apparatus. Therefore, the present invention makes it practical to integrate the manufacturing process of full color display panels of organic electroluminescent display apparatus, thereby reducing the manufacture cost and time. In addition, the organic electroluminescent devices prepared from the 9,10-bis[2-(p-substituted phenyl)pyrimidin-4-yl] anthracene compounds according to the present invention have a higher luminous efficiency. Further, the process for preparing the 9,10-bis[2-(p-substituted phenyl)pyrimidin-4-yl] anthracene compounds according to the present invention is simple and easy to be implemented.

It should be understood that this invention is not intended to be limited to the embodiments set forth above for illustrative purposes. Various modifications and alterations of this invention will be apparent to those skilled in the art without departing from the scope and spirit of this invention. Such modifications and alterations are included in the scope of the invention.

What is claimed is:

1. A 9,10-bis[2-(p-substituted phenyl)pyrimidin-4-yl] anthracene compound, characterized by having the following formula:

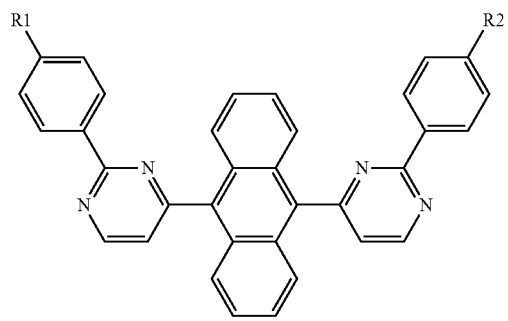

wherein R1 and R2, which is identical or different, are each individually selected from:
hydrogen, carboxyl, cyano, nitro,
paraffinic alkyl having 1 to 20 carbon atoms,
cyclic alkyl having 3 to 20 carbon atoms,
paraffinic alkoxyl having 1 to 20 carbon atoms,
aromatic hydrocarbyl having 6 to 50 ring carbon atoms,
aryloxy having 5 to 50 ring atoms, and
an ester group having 2 to 20 carbon atoms.

2. The compound according to claim 1, characterized in that R1 and R2 are each individually selected from:
C1-C20 paraffinic alkyl, optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;
C3-C20 cyclic alkyl, optionally substituted by 1 to 3 substituents selected from C1-C4 alkyl, hydroxyl, halogen, amino, carboxyl, cyano and nitro;
C1-C20 paraffinic alkyl-O—, in which the C1-C20 paraffinic alkyl is optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;
aromatic hydrocarbyl having 6 to 50 ring carbon atoms, optionally substituted by C1-C4 linear or branched alkyl, or by phenyl substituted with C1-C4 linear or branched alkyl;
aromatic hydrocarbonoxy having 6 to 50 ring carbon atoms, in which the aromatic hydrocarbon carbon ring is optionally substituted by C1-C4 linear or branched alkyl, or by phenyl substituted with C1-C4 linear or branched alkyl;
heteroaromatic hydrocarbonoxy having 5 to 50 ring atoms, in which the heteroaromatic hydrocarbon ring comprises at least one unsaturated double bond and heteroatom selected from O, N and S, and the ring carbon atom of the heteroaromatic hydrocarbon ring is optionally substituted by C1-C4 linear or branched alkyl, or by phenyl substituted with C1-C4 linear or branched alkyl; and C1-C19 alkyl-OC(O)—, in which the C1-C19 alkyl is linear, branched, or cyclic alkyl optionally substituted by 1 to 3 substituents selected from hydroxyl, halogen, amino, carboxyl, cyano and nitro.

3. The compound according to claim 2, characterized in that the aromatic hydrocarbyl having 6 to 50 ring carbon atoms is selected from phenyl, a polybenzene ring group in which 2-8 benzene rings are connected by single bond(s), or a fused ring group in which 2-10 benzene rings are fused at two or more positions;

the aromatic hydrocarbyl of the aromatic hydrocarbonoxy having 6 to 50 ring carbon atoms is selected from phenyl, a polybenzene ring group in which 2-8 benzene rings are connected by single bond(s), or a fused ring group in which 2-10 benzene rings are fused at two or more positions; and the heteroaromatic hydrocarbon ring of the heteroaromatic hydrocarbonoxy having 5 to 50 ring atoms comprises one or two heteroatom(s) selected from O, N and S and at least two unsaturated double bonds.

4. The compound according to claim 2, characterized in that R1 and R2 are each individually selected from:

C1-C12 linear alkyl or C3-C12 branched alkyl, optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;

C3-C12 cyclic alkyl, optionally substituted by 1 to 3 substituents selected from C1-C4 alkyl, hydroxyl, halogen, amino, carboxyl, cyano and nitro;

C1-C12 paraffinic alkyl-O—, in which the C1-C12 paraffinic alkyl is optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;

aromatic hydrocarbyl having 6 to 30 ring carbon atoms selected from phenyl, a polybenzene group in which 2-5 benzene rings are connected by single bond(s), or a fused group in which 2-8 benzene rings are fused at two or more positions, wherein the phenyl, the polybenzene group or the fused group is optionally substituted by C1-C4 linear or branched alkyl;

aromatic hydrocarbonoxy having 6 to 30 ring carbon atoms, in which the aromatic hydrocarbyl is selected from phenyl, a polybenzene group in which 2-5 benzene rings are connected by single bond(s), or a fused group in which 2-8 benzene rings are fused at two or more positions, wherein the phenyl, the polybenzene group or the fused group is optionally substituted by C1-C4 linear or branched alkyl;

heteroaromatic hydrocarbonoxy having 5 to 20 ring atoms, in which the heteroaromatic hydrocarbon ring comprises one or two heteroatom(s) selected from O, N and S and at least two unsaturated double bonds, and the ring carbon atom of the heteroaromatic hydrocarbon ring is optionally substituted by C1-C4 linear or branched alkyl; and C1-C12 alkyl-OC(O)—, in which the C1-C12 alkyl is linear, branched, or cyclic alkyl optionally substituted by 1 to 3 substituents selected from hydroxyl, halogen, amino, carboxyl, cyano and nitro.

5. The compound according to claim 4, characterized in that R1 and R2 are each individually selected from:

C1-C8 linear alkyl or C3-C8 branched alkyl, optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;

C3-C8 cyclic alkyl, optionally substituted by 1 to 3 substituents selected from C1-C4 alkyl, hydroxyl, halogen, amino, carboxyl, cyano and nitro;

C1-C8 paraffinic alkyl-O—, in which the C1-C8 paraffinic alkyl is optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;

phenyl, a polybenzene group in which 2-4 benzene rings are connected by single bond(s), or a fused group in which 2-5 benzene rings are fused at two or more positions, wherein the phenyl, the polybenzene group or the fused group is optionally substituted by C1-C4 linear or branched alkyl;

phenyl-O—, a polybenzene group-O—, or a fused group-O—, wherein the polybenzene group is a group in which 2-4 benzene rings are connected by single bond(s), the fused group is a group in which 2-5 benzene rings are fused at two or more positions, and the phenyl, the polybenzene group or the fused group is optionally substituted by C1-C4 linear or branched alkyl;

heteroaromatic hydrocarbonoxy having 5 to 14 ring atoms, in which the heteroaromatic hydrocarbon ring comprises one or two heteroatom(s) selected from O, N and S and at least two unsaturated double bonds, and the ring carbon atom of the heteroaromatic hydrocarbon ring is optionally substituted by C1-C4 linear or branched alkyl; and C1-C8 alkyl-OC(O)—, in which the C1-C8 alkyl is linear, branched, or cyclic alkyl optionally substituted by 1 to 3 substituents selected from hydroxyl, halogen, amino, carboxyl, cyano and nitro.

6. The compound according to claim 5, characterized in that R1 and R2 are each individually selected from:

C1-C6 linear alkyl or C3-C6 branched alkyl, optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;

C3-C6 cyclic alkyl, optionally substituted by 1 to 3 substituents selected from C1-C4 alkyl, hydroxyl, halogen, amino, carboxyl, cyano and nitro;

C1-C6 paraffinic alkyl-O—, in which the C1-C6 paraffinic alkyl is optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;

aromatic hydrocarbyl selected from phenyl, naphthyl, fluorenyl, anthryl, naphthacenyl, phenanthryl, perylenyl, picenyl, pyrenyl, biphenyl, terphenyl, and quaterphenyl, wherein the aromatic hydrocarbyl is optionally substituted by C1-C4 linear or branched alkyl;

aromatic hydrocarbonoxy selected from phenyl-O—, naphthyl-O—, fluorenyl-O—, anthryl-O—, naphthacenyl-O—, phenanthryl-O—, perylenyl-O—, picenyl-O—, pyrenyl-O—, biphenyl-O—, terphenyl-O—, and quaterphenyl-O—, wherein the aromatic hydrocarbonoxy is optionally substituted by C1-C4 linear or branched alkyl;

heteroaromatic hydrocarbonoxy selected from pyrrolyl-O—, pyridinyl-O—, indolyl-O—, furanyl-O—, pyranyl-O—, benzofuranyl-O—, quinolyl-O—, quinoxalinyl-O—, carbazolyl-O—, phenanthridinyl-O—, acridinyl-O—, phenanthrolyl-O—, phenazinyl-O—, phenothiazinyl-O—, and phenoxazinyl-O—, wherein the heteroaromatic hydrocarbonoxy is optionally substituted by C1-C4 linear or branched alkyl; and C1-C6 alkyl-OC(O)—, in which the C1-C6 alkyl is linear, branched, or cyclic alkyl optionally substituted by 1 to 3 substituents selected from hydroxyl, halogen, amino, carboxyl, cyano and nitro.

7. The compound according to claim 2, characterized in that the C1-C20 paraffinic alkyl is any one of methyl, ethyl, propyl, isopropyl, n-butyl, sec-butyl, isobutyl, tert-butyl, n-pentyl, n-hexyl, n-heptyl, n-octyl; or any one of hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-tert-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-tert-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-tert-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-tert-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-tert-butyl, 1,2,3-triaminopropyl, benzyl, 1-phenylethyl, 2-phenylethyl, 1-phenylisopropyl, 2-phenylisopropyl, phenyl-tert-butyl, α-naphthylmethyl, 1-α-naphthylethyl, 2-α-naphthylethyl, 1-α-naphthylisopropyl, 2-α-naphthylisopropyl, 3-naphthylmethyl, 1-β-naphthylethyl, 2-3-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-chloro-2-phenylisopropyl, and triphenylmethyl;

the C3-C20 cyclic alkyl is any one of cyclopropyl, cyclobutyl, cyclopentyl, cyclohexyl, adamantyl, norbornyl, cycloeicosyl, 2-fluorocyclopropyl, 3-hydroxycyclobutyl, 3-aminocyclopentyl, 4-methylcyclohexyl, and 1,2,3-tribromoadamantyl;

the paraffinic alkyl of the C1-C20 paraffinic alkyl-O— is any one of methyl, ethyl, propyl, isopropyl, n-butyl, sec-butyl, isobutyl, tert-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dichloroisopropyl, 2,3-dichloro-tert-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-tert-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-tert-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-tert-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-tert-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-tert-butyl, and 1,2,3-trinitropropyl;

the aromatic hydrocarbyl having 6 to 50 ring carbon atoms or the aromatic hydrocarbyl of the aromatic hydrocarbonoxy having 6 to 50 ring carbon atoms is any one of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenyl, 3-biphenyl, 4-biphenyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthryl, 4-methyl-biphenyl, and 4'-tert-butyl-p-terphenyl-4-yl;

the heteroaromatic hydrocarbyl of the heteroaromatic hydrocarbonoxy having 5 to 50 ring atoms is any one of 2-pyrrolyl, 3-pyrrolyl, 5-pyridinyl, 6-pyridinyl, 2-pyridinyl, 3-pyridinyl, 4-pyridinyl, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-furanyl, 3-furanyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalyl, 5-quinoxalyl, 6-quinoxalyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthrolin-2-yl, 1,7-phenanthrolin-3-yl, 1,7-phenanthrolin-4-yl, 1,7-phenanthrolin-5-yl, 1,7-phenanthrolin-6-yl, 1,7-phenanthrolin-8-yl, 1,7-phenanthrolin-9-yl, 1,7-phenanthrolin-10-yl, 1,8-phenanthrolin-2-yl, 1,8-phenanthrolin-3-yl, 1,8-phenanthrolin-4-yl, 1,8-phenanthrolin-5-yl, 1,8-phenanthrolin-6-yl, 1,8-phenanthrolin-7-yl, 1,8-phenanthrolin-9-yl, 1,8-phenanthrolin-10-yl, 1,9-phenanthrolin-2-yl, 1,9-phenanthrolin-3-yl, 1,9-phenanthrolin-4-yl, 1,9-phenanthrolin-5-yl, 1,9-phenanthrolin-6-yl, 1,9-phenanthrolin-7-yl, 1,9-phenanthrolin-8-yl, 1,9-phenanthrolin-10-yl, 1,10-phenanthrolin-2-yl, 1,10-phenanthrolin-3-yl, 1,10-phenanthrolin-4-yl, 1,10-phenanthrolin-5-yl, 2,9-phenanthrolin-1-yl, 2,9-phenanthrolin-3-yl, 2,9- phenanthrolin-4-yl, 2,9-phenanthrolin-5-yl, 2,9-phenanthrolin-6-yl, 2,9-phenanthrolin-7-yl, 2,9-phenanthrolin-8-yl, 2,9-phenanthrolin-10-yl, 2,8-phenanthrolin-1-yl, 2,8-phenanthrolin-3-yl, 2,8-phenanthrolin-4-yl, 2,8-phenanthrolin-5-yl, 2,8-phenanthrolin-6-yl, 2,8-phenanthrolin-7-yl, 2,8-phenanthrolin-9-yl, 2,8-phenanthrolin-10-yl, 2,7-phenanthrolin-1-yl, 2,7-phenanthrolin-3-yl, 2,7-phenanthrolin-4-yl, 2,7-phenanthrolin-5-yl, 2,7-phenanthrolin-6-yl, 2,7-phenanthrolin-8-yl, 2,7-phenanthrolin-9-yl, 2,7-phenanthrolin-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, and 4-tert-butyl-3-indolyl; and the C1-C19 alkyl-OC(O)— is any one of methyl ester group, ethyl ester group, propyl ester group, isopropyl ester group, n-butyl ester group, sec-butyl ester group, isobutyl ester group, n-pentyl ester group, n-hexyl ester group, n-heptyl ester group, and n-octyl ester group.

8. An organic electroluminescent device, comprising a cathode, an anode, and a light-emitting layer arranged between said cathode and anode, characterized in that said light-emitting layer comprises a 9,10-bis[2-p-substituted phenyl)pyrimidin-4-yl] anthracene compound having the following formula:

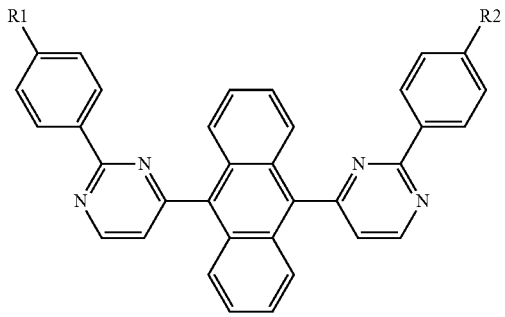

wherein R1 and R2, which is identical or different, are each individually selected from:
hydrogen, carboxyl, cyano, nitro,
paraffinic alkyl having 1 to 20 carbon atoms,
cyclic alkyl having 3 to 20 carbon atoms,
paraffinic alkoxyl having 1 to 20 carbon atoms,
aromatic hydrocarbyl having 6 to 50 ring carbon atoms,
aryloxy having 5 to 50 ring atoms, and
an ester group having 2 to 20 carbon atoms.

9. The organic electroluminescent device according to claim 8, characterized in that said organic electroluminescent device further comprises a hole transport layer and an electron transport layer, wherein the hole transport layer is arranged between the anode and the light-emitting layer, and the electron transport layer is arranged between the cathode and the light-emitting layer.

10. An organic electroluminescent display apparatus, characterized by comprising an organic electroluminescent device comprising a cathode, an anode, and a light-emitting layer arranged between said cathode and anode, wherein said light-emitting layer comprises a 9,10-bis[2-p-substituted phenyl)pyrimidin-4-yl] anthracene compound having the following formula:

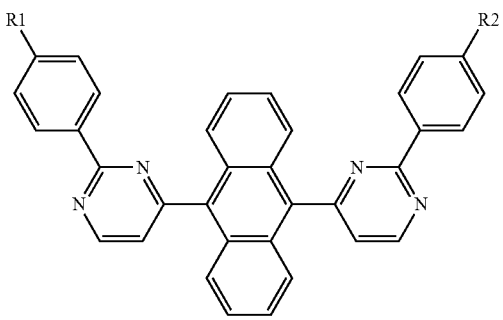

wherein R1 and R2, which is identical or different, are each individually selected from:
hydrogen, carboxyl, cyano, nitro,
paraffinic alkyl having 1 to 20 carbon atoms,
cyclic alkyl having 3 to 20 carbon atoms,
paraffinic alkoxyl having 1 to 20 carbon atoms,
aromatic hydrocarbyl having 6 to 50 ring carbon atoms,
aryloxy having 5 to 50 ring atoms, and
an ester group having 2 to 20 carbon atoms.

11. A method of preparing a 9,10-bis[2-(p-substituted phenyl)pyrimidin-4-yl] anthracene compound having the following formula:

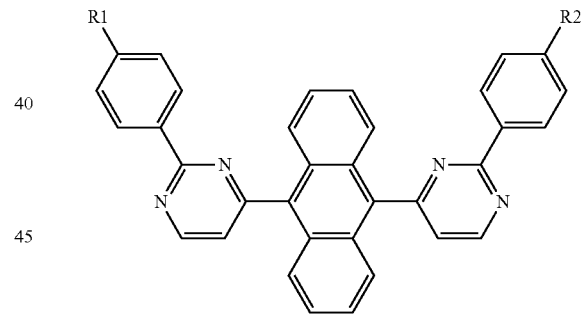

wherein R1 and R2, which is identical or different, are each individually selected from:
hydrogen, carboxyl, cyano, nitro,
paraffinic alkyl having 1 to 20 carbon atoms, optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;
cyclic alkyl having 3 to 20 carbon atoms, optionally substituted by 1 to 3 substituents selected from C1-C4 alkyl, hydroxyl, halogen, amino, carboxyl, cyano and nitro;
paraffinic alkoxyl having 1 to 20 carbon atoms, in which the paraffinic alkyl is optionally substituted by 1 to 3 substituents selected from hydroxyl, halogen, amino, carboxyl, cyano, nitro, pyrrolyl, naphthyl, and substituted or unsubstituted phenyl, wherein the substituted phenyl refers to a benzene ring substituted by methyl, hydroxyl, halogen, amino, carboxyl, cyano or nitro;

aromatic hydrocarbyl having 6 to 50 ring carbon atoms, optionally substituted by C1-C4 linear or branched alkyl, or by phenyl substituted with C1-C4 linear or branched alkyl;

aromatic hydrocarbonoxy having 6 to 50 ring carbon atoms, in which the aromatic hydrocarbon carbon ring is optionally substituted by C1-C4 linear or branched alkyl, or by phenyl substituted with C1-C4 linear or branched alkyl;

heteroaromatic hydrocarbonoxy having 5 to 50 ring atoms, in which the heteroaromatic hydrocarbon ring comprises at least one unsaturated double bond and heteroatom selected from O, N and S, and the ring carbon atom of the heteroaromatic hydrocarbon ring is optionally substituted by C1-C4 linear or branched alkyl, or by phenyl substituted with C1-C4 linear or branched alkyl; and an ester group having 2 to 20 carbon atoms and represented by C1-C19 alkyl-OC(O)—, in which the C1-C19 alkyl is linear, branched, or cyclic alkyl optionally substituted by 1 to 3 substituents selected from hydroxyl, halogen, amino, carboxyl, cyano and nitro;

characterized in that, when R1 and R2 are different, the method comprises the following steps:

Reaction step 1: reacting p-R1-benzamide or p-R2-benzamide with formamide respectively to produce intermediates 1 and 2:

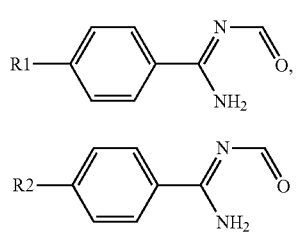

Intermediate 1

Intermediate 2 wherein, R1 and R2 are defined as above, and R1 and R2 are different; and

Reaction step 2: reacting 9,10-diacetylanthracene with the intermediates 1 and 2 to produce said 9,10-bis[2-(p-substituted phenyl)pyrimidin-4-yl] anthracene compound; or when R1 and R2 are the same, the method comprises the following steps:

Reaction step 1': reacting p-R-benzamide with formamide to produce an intermediate M:

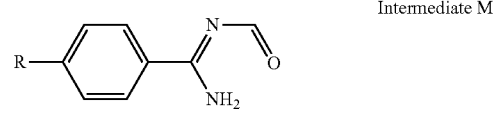

Intermediate M wherein, R1 and R2 are defined as above, and R1=R2=R; and

Reaction step 2': reacting 9,10-diacetylanthracene with the intermediate M to produce said 9,10-bis[2-(p-substituted phenyl)pyrimidin-4-yl] anthracene compound.

12. The method according to claim 11, characterized in that the method further comprises a step of separating and purifying the raw product of Reaction step 2 or 2'.

13. The method according to claim 11, characterized in that, in Reaction step 1 or 1', the mole ratio of the p-R1-benzamide, p-R2-benzamide or p-R-benzamide to formamide is 1:(1-1.5), respectively; reaction temperature is in the range of 50 to 150° C., and reaction time is in the range of 2 to 24 h;

in Reaction step 2 or 2', the mole ratio of 9,10-diacetylanthracene to the intermediates 1 and 2 is 1:(1-1.5):(1-1.5), or the mole ratio of 9,10-diacetylanthracene to the intermediate M is 1:(2-3); reaction temperature is in the range of 50 to 150° C., and reaction time is in the range of 2 to 24 h.

14. The method according to claim 12, characterized in that the separating and purifying step comprises:

acidifying the raw product and then extracting to obtain a first extract liquor;

alkalifying the first extract liquor and then extracting to obtain a second extract liquor; and separating the second extract liquor by a chromatographic column to obtain a purified 9,10-bis[2-(p-substituted phenyl)pyrimidin-4-yl] anthracene compound.

* * * * *